(12) United States Patent
Jaeckel et al.

(10) Patent No.: US 11,174,473 B2
(45) Date of Patent: *Nov. 16, 2021

(54) VARIANTS OF CHYMOSIN WITH IMPROVED PROPERTIES

(71) Applicant: Chr. Hansen A/S, Hoersholm (DK)

(72) Inventors: Christian Jaeckel, Vaerloese (DK); Martin Lund, Copenhagen (DK); Enikö Fodor Hansen, Helsingoer (DK); Lone Riisberg, Nivaa (DK); Iben Jeppesen, Alleroed (DK); Johannes Maarten Van Den Brink, Herlev (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/738,562

(22) PCT Filed: Jun. 22, 2016

(86) PCT No.: PCT/EP2016/064414
§ 371 (c)(1),
(2) Date: Dec. 20, 2017

(87) PCT Pub. No.: WO2016/207214
PCT Pub. Date: Dec. 29, 2016

(65) Prior Publication Data
US 2018/0187179 A1    Jul. 5, 2018

(30) Foreign Application Priority Data
Jun. 22, 2015  (EP) ..................... 15173099

(51) Int. Cl.
*C12N 9/64* (2006.01)
*C12N 15/00* (2006.01)
(Continued)

(52) U.S. Cl.
CPC ........... *C12N 9/6483* (2013.01); *C12N 15/52* (2013.01); *A23C 19/0326* (2013.01); *C12Y 304/23004* (2013.01)

(58) Field of Classification Search
CPC .................................................. C12N 9/6483
See application file for complete search history.

(56) References Cited

U.S. PATENT DOCUMENTS 7,390,936 B1    6/2008  Rooijen et al.
7,482,148 B2    1/2009  Mule et al.
(Continued)

FOREIGN PATENT DOCUMENTS

EP    0 123 928 A2    11/1984
JP    2010-046034 A    3/2010
(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Foley & Lardner LLP

(57) ABSTRACT

Variants of chymosin with improved properties.

24 Claims, 4 Drawing Sheets

Figure 2:
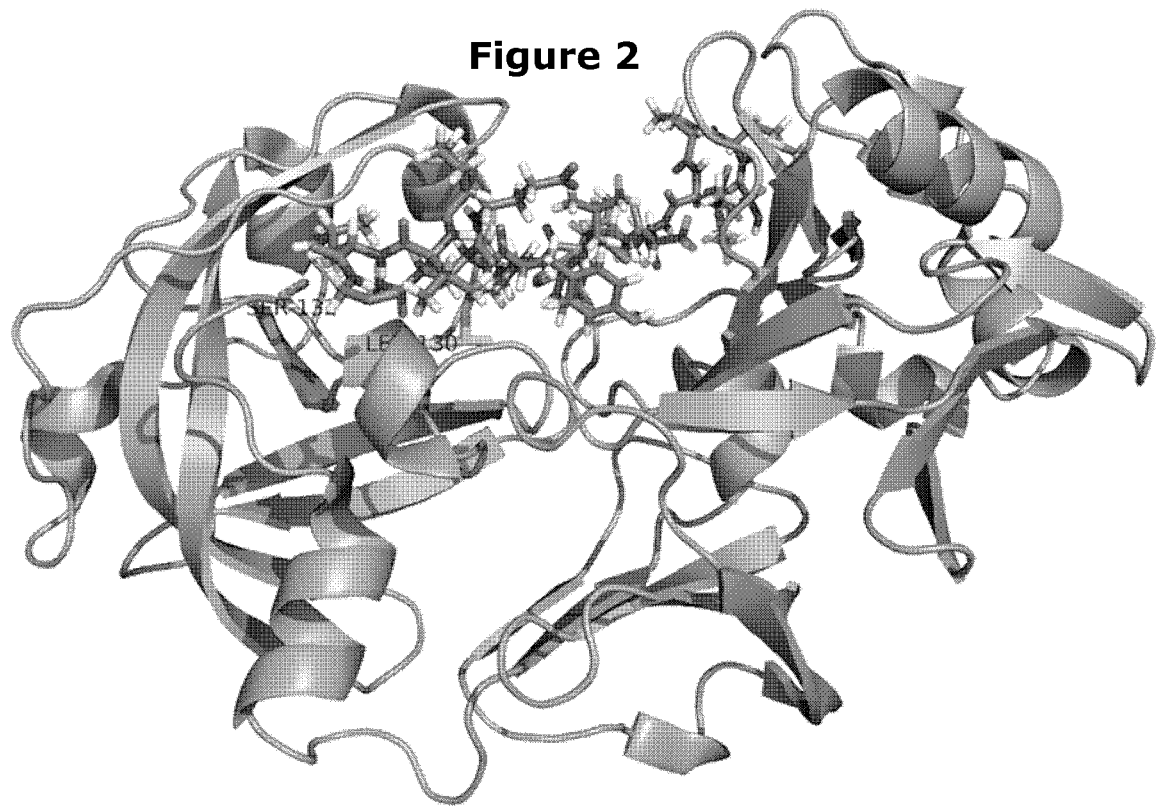

Specification includes a Sequence Listing.

(51) Int. Cl.
C12N 15/52 (2006.01)
A23C 19/032 (2006.01)

(56) References Cited

U.S. PATENT DOCUMENTS

| | | | |
|---|---|---|---|
| 9,930,899 | B2* | 4/2018 | Van Den Brink ... A23C 9/1209 |
| 10,167,463 | B2 | 1/2019 | Dekker et al. |
| 2008/0226768 | A1 | 9/2008 | Kappeler et al. |
| 2011/0287137 | A1 | 11/2011 | Kappeler et al. |
| 2017/0067041 | A1 | 3/2017 | Van Den Brink et al. |
| 2018/0110234 | A1 | 4/2018 | Faiveley et al. |
| 2018/0251747 | A1 | 9/2018 | Jaeckel et al. |
| 2018/0317510 | A1 | 11/2018 | Van Den Brink et al. |
| 2019/0116821 | A1 | 4/2019 | Jaeckel et al. |
| 2019/0174783 | A1 | 6/2019 | Jaeckel et al. |

FOREIGN PATENT DOCUMENTS

| | | | | |
|---|---|---|---|---|
| JP | 2010-099082 A | 5/2010 | | |
| JP | 2011-182794 A | 9/2011 | | |
| RU | 2 192 137 C2 | 11/2002 | | |
| WO | WO 2002/36752 A2 | 5/2002 | | |
| WO | WO 2004/031733 A2 | 4/2004 | | |
| WO | WO 2005/003345 A2 | 1/2005 | | |
| WO | WO 2008/098973 | 8/2008 | | |
| WO | WO 2010/110464 A1 | 9/2010 | | |
| WO | WO 2013/164479 A2 | 11/2013 | | |
| WO | WO 2013/174840 A1 | 11/2013 | | |
| WO | WO-2013164481 A1 * | 11/2013 | ........... | A23C 19/072 |
| WO | WO 2015/128417 A1 | 9/2015 | | |
| WO | WO-2016/207214 A1 | 12/2016 | | |
| WO | WO-2017/037092 A1 | 3/2017 | | |

OTHER PUBLICATIONS

U.S. Appl. No. 16/302,584, filed Nov. 16, 2018, Chr. Hansen A/S.
U.S. Appl. No. 16/302,590, filed Nov. 16, 2018, Chr. Hansen A/S.
Jensen, et al., "Camel and bovine chymosin: the relationship between their structures and cheese-making properties," *Acta Cryst.*, D69, pp. 901-913 (May 2013).
Møller, et al., "Camel and Bovine Chymosin Hydrolysis of Bovine $\alpha_{s1}$- and β-Caseins Studied by Comparative Peptide Mapping," *Journ. of Agriculture and Food Chemistry*, vol. 60, No. 45, pp. 11421-11432 (Nov. 2012).
Børsting, et al., "Impact of selected coagulants and starts on primary proteolysis and amino acid release related to bitterness and structure of reduced-fat Cheddar Cheese," *Dairy Sci, & Technol.*, vol. 92. pp. 593-612 (Oct. 2012).
McSweeney, "Biochemistry of cheese ripening." *Int. J. Dairy Technol.*, vol. 57, No. 2/3, pp. 127-144 (May/Aug. 2004).
Gilliland, et al., The Three-Dimensional Structure of Recombinant Bovine Chymosin at 2,3 Å Resolution,: *Proteins: Structure, Function, and Genetics*, vol. 8, pp. 82-101 (Jan. 1990).
Palmer, et al., "Bovine Chymosin: A Computational Study of recognition and Binding of Bovine k-Casein," *Biochemistry*, vol. 49, pp. 2563-2573 (Feb. 2010).
Sorensen, et al., "Hot-Spot Maping of the Interactions between Chymosin and Bovine k-Casein," *Journ. of Agric. and Food Chem.*, vol. 60, pp. 7949-7959 (Jul. 2013).
Schechter, et al., "On the Size of the Active Site in Proteases. I. Papain," vol. 27, No. 2, pp. 157-162 (Mar. 1967).
Bansal, et al., "Suitability of recombinant camel (*Camelus dromedaries*) chymosin as a coagulant for Cheddar Cheese," *Intern. Dairy Journ.*, vol. 19, pp. 510-517 (Mar. 2009).
Kumar, et al., "Chymosin and other milk coagulants: sources and biotechnological interventions," *Critical Reviews in Biotechnology*, vol. 30, No. 4, pp. 243-258 (Mar. 2010).
Creamer et al., "Rheological Evaluation of Maturing Cheddar," *Journ. of Food Science*, vol. 47, No. 2, pp. 631-636 (Mar. 1982).
Moynihan, et al., "Effect of camel chymosin on the texture, functionality, and sensory properties of low-moisture, part-skim Mozzarella cheese," *J. Dairy Sci.*, vol. 97, pp. 85-96 (Sep. 2013).

Ehren, et al., "Protein engineering of improved prolyl endopeptidases for celiac sprue therapy," *Protein Engineering, Design & Selection*, vol. 21, No. 12, pp. 699-707 (2008).
Chitpinityol et al., "Site-specific mutations of calf chymosin B which influence milk-clotting activity," *Food Chemistry*, vol. 62, No. 2, pp. 133-139 (Jun. 1998).
Newman et al., "X-ray Analyses of Aspartic Proteinases IV, Structure and Refinement at 2.2 Å Resolution of Bovine Chymosin," *J. Mol. Biol.*, vol. 221, pp. 1295-1309 (May 1991).
Gustchina, et al., "Post X-ray crystallographic studies of chymosin: the existence of two structural forms and the regulation of activity by the interaction with the histidine-proline cluster of k-casein," *FEBS Letters*, vol. 379, pp. 60-62 (Jan. 1996).
Visser, et al., "Peptide substrates for chymosin (rennin). Interaction sites in k-casein-related sequences located outside the (103-108)-hexapeptide region that fits into the enzyme's active-site cleft," *Biochem. J.*, vol. 244, pp. 553-558 (Jun. 1987).
Govindarajan, et al., "Mapping of Amino Acid Substitutions Conferring Herbicide Resistance in Wheat Glutathione Transferase," *ACS Synth. Biol.*, vol. 4, No. 3, pp. 221-227 (Jun. 2014).
U.S. Appl. No. 61/642,095, filed May 3, 2012, Dekker et al.
Albert et al., "Protein Engineering Aspartic Proteinases: Site-Directed Mutagenesis, Biochemical Characterisation, and X-Ray Analysis of Chymosins with Substituted Single Amino Acid Substitutions and Loop Replacements," in Aspartic Proteinases, Chapter 23, pp. 169-178 (1998) (James, ed.).
Claverie-Martin et al., "Aspartic Proteases Used in Cheese Making," in Industrial Enzymes pp. 207-219 (2007) (J. Polaina and A.P. MacCabe, eds.).
Chen et al., "Functional Implications of Disulfide Bond, Cys206-Cys210, in Recombinant Prochymosin (Chymosin)," Biochemistry 2000, 39, 12140-12148 (Published online Sep. 2000).
Kappeler et al. "Compositional and Structural Analysis of Camel Milk Proteins with Emphasis on Protective Proteins," ETH Zurich Research Collection, Dissertation, ETH No. 12947, pp. 1-137 (1998).
Moller et al., "Comparison of the Hydrolysis of Bovin k-Casein by Camel and Bovine Chymosin: A Kinetic and Specificity Study," Journal of Agricultural and Food Chemistry, 60(21):5454-5460 (May 2012) (with NCBI extract).
Filippovich et al. "Radicals," pp. 38-43 (2005).
Visser et al., "Peptide substrates for chymosin (rennin)" Biochem. J. (1987) vol. 244, pp. 553-558.
Beppu,et al., "Modification of Milk-clotting aspartic proteases, chymosin and mucor rennin," *GBF Monographs*, pp. 87-92 (Dec. 1989).
Brenden et al., "Introduction to Protein Structure," Garland Publishing., Inc. New York, p. 247, 1991.
Database UniProt [Online] Oct. 1, 2000 (Oct. 1, 2000),"SubName: Full=Prochymosin {ECO:0000313|EMBL:AAF27315.1};", retrieved from EBI accession No. UNIPROT:Q9N1P5 Database accession No. Q9N1P5.
Database UniProt [Online] Feb. 5, 2008 (Feb. 5, 2008), "SubName: Full=Preprochymosin b {ECO:0000313|EMBL:ABX55935.1}; EC=3. 4.23.4 {ECO:0000313|EMBL:ABX55935.1};", retrieved from EBI accession No. UNIPROT:A9LY78 Database accession No. A9LY78; -& Juan Andres.
Database UniProt [Online] Nov. 1, 1990 (Nov. 1, 1990), "RecName: Full=Chymosin; EC=3.4.23.4; AltName: Full=Preprorennin; Flags: Precursor;", retrieved from EBI accession No. UNIPROT:P18276 Database accession No. P18276 ; -& J. Pungercar et al: "Complete primary structure of lamb preprochymosin deduced from cDNA", Nucleic Acids Research, vol. 18, No. 15, Aug. 11, 1990 (Aug. 11, 1990), pp. 4602-4602, XP055314297, GB ISSN: 0305-1048, DOI: 10.1093/nar/18.15.4602.
Database UniProt [Online] Mar. 20, 2007 (Mar. 20, 2007), "SubName: Full=Preprochymosin {ECO:0000313|EMBL:ABN13683.1};", retrieved from EBI accession No. UNIPROT:A3F4M4 Database accession No. A3F4M4.
Database Geneseq [Online] Jan. 2, 2014 (Jan. 2, 2014), "Bovine derived mature chymosin B variant H76Q.", retrieved from EBI

(56) References Cited

OTHER PUBLICATIONS accession No. GSP:BAY37837 Database accession No. BAY37837; -& WO 2013/164479 A2 (DSM IP Assets BV [NL]) Nov. 7, 2013 (Nov. 7, 2013).

Lindblad-Toh et al., E2R9E5_CANLF. UnitProtKB Database. 2014.

Houen, et al., "The Primary Structure and Enzymic Properties of Porcine Prochymosin and Chymosin," *Int. J. Biochem. Cell Biol.*, vol. 28, No. 6, pp. 667-675 (1996).

Kageyama, "New World Monkey Pepsinogens A and C, and Prochymosins, Purification, Characterization of Enzymatic Properties, cDNA Cloning, and Molecular Evolution," *Journal of Biochemistry*, vol. 127, pp. 761-770 (Feb. 2000).

Kappeler et al., "Characterization of recombinant camel chymosin reveals superior properties for the coagulation of bovine and camel milk," Biochemical and Biophysical Research Communications, 342 (2006) 647-654.

Lavallie, "Production of Recombinant Proteins in *Escherichia coli*," Current Protocols in Protein Science (1995) 5.1.1-5.1.8.

Lindblad-Toh et al., "Genome sequence, comparative analysis and haplotype structure of the domestic dog," Nature 438: 803-819 (Dec. 2005).

Pitts et al.; "Expression and characterisation of chymosin pH optima mutants produced in *Trichoderma reesei*"; *Journal of Biotechnology*, 28(1): 69-83 (Mar. 1993).

Preprochymosin b, A9LY78,UniProt, May 16, 2012, [searched on Mar. 17, 2017]. URL: https://www.uniprot.org/A9LY78.txt?version=21.

Pungerčar et al., "Complete primary structure of lamb prepochymosin deduced from cDNA," Nucleic Acids Research, vol. 18, No. 15:4602 (Aug. 1990).

Sambrook et al., Molecular Cloning, 1989, Cold Spring Harbor Laboratory Press, pp. 8.46-8.52 and pp. 11.2-11.19.

Strop et al.; "Engineering Enzyme Subsite Specificity: Preparation, Kinetic Characterization, and X-ray Analysis at 2.0-Å Resolution of Val111Phe Site-Mutated Calf Chymosin"; *Biochemistry*, 29: 9863-9871 (Oct. 1990).

Suzuki et al.; "Alteration of catalytic properties of chymosin by site-directed mutagenesis"; *Protein Engineering*, 2(7): 563-569 (May 1989).

Suzuki et al.; "Site-directed mutagenesis reveals functional contribution of Thr218, Lys220 and Asp 304 in chymosin"; *Protein Engineering*, 4(1): 69-71 (Oct. 1990).

Vallejo et al., "Cloning and Expression of Buffalo Active Chymosin in Pichia pastoris," *J. Agric. Food Chem.*, vol. 56, No. 22, pp. 10606-10610 (Nov. 2008).

Van Den Brink et al.; "Increased production of chymosin by glycosylation"; *Journal of Biotechnology*, 125(2): 304-310 (Sep. 2006)(published online Apr. 2006).

Williams et al.; "Mutagenesis, biochemical characterization and X-ray structural analysis of point mutants of bovine chymosin"; *Protein Engineering*; 10(9): 991-997 (Sep. 1997).

Zhang et al.; "Functional implications of disulfide bond, Cys45-Cys50, in recombinant prochymosin"; *Biochimica et Biophysica Acta*, 1343(2): 278-286 (Dec. 1997).

V. V. Starovoitova et al. "Comparative Investigation of Functional Properties of Calf Chymosin and its Recombinant Forms," Biohimiya, 2006, tom 71, vyp. 3, s. 402-407 (in Russian).

\* cited by examiner

Figure 1

```
                           1                                                                    50
       Bos_bovis_chymosin_B MRCLVVLLAV FALSQGAEIT RIPLYKGKSL RKALKEHGLL EDFLQKQQYG
                     Sheep MRCLVVLLAV FALSQGAEIT RIPLYKGKPL RKALKERGLL EDFLQKQQYG
              C._bactrianus MRCLVVLLAA LALSQASGIT RIPLHKGKTL RKALKERGLL EDFLQRQQYA
         Camelus_dromedarius MRCLVVLLAA LALSQASGIT RIPLHKGKTL RKALKERGLL EDFLQRQQYA
                       Pig .IRGRVLLAV LALSQGSGIT RVPLRKGKSL RKELKERGLL EDFLQKQPYA
                       Rat MRCFVLLLAV LAIAQSHVVT RIPLHKGKSL RNTLKEQGLL EDFLRRHQYE 51                                                                   100
       Bos_bovis_chymosin_B ISSKYSGFGE VASVPLTNYL DSQYFGKIYL GTPPQEFTVL FDTGSSDFWV
                     Sheep VSSEYSGFGE VASVPLTNYL DSQYFGKIYL GTPPQEFTVL FDTGSSDFWV
              C._bactrianus VSSKYSSLGK VAREPLTSYL DSQYFGKIYI GTPPQEFTVV FDTGSSDLWV
         Camelus_dromedarius VSSKYSSLGK VAREPLTSYL DSQYFGKIYI GTPPQEFTVV FDTGSSDLWV
                       Pig LSSKYSSFGE VASEPLTNYL DTQYFGKIYI GTPPQEFTVV FDTGSSELWV
                       Rat FSEKNSNIGM VASEPLTNYL DSEYFGLIYV GTPPQEFKVV FDTGSSELWV 101                                                                  150
       Bos_bovis_chymosin_B PSIYCKSNAC KNHQRFDPRK SSTFQNLGKP LSIHYGTGSM QGILGYDTVT
                     Sheep PSIYCKSNAC KNHQRFDPRK SSTFQNLGKP LSIRYGTGSM QGILGYDTVT
              C._bactrianus PSIYCKSNAC KNHHRFDPRK SSTFRNLGKP LSIHYGTGSI EGFLGYDTVT
         Camelus_dromedarius PSIYCKSNVC KNHHRFDPRK SSTFRNLGKP LSIHYGTGSM EGFLGYDTVT
                       Pig PSVYCKSDAC QNHHRFNPSK SSTFQNLDKP LSIQYGTGSI QGFLGYDTVM
                       Rat PSVYCSSKVC RNHNRFDPSK SFTFQNLSKP LFVQYGTGSV EGFLAYDTVT 151                                                                  200
       Bos_bovis_chymosin_B VSNIVDIQQT VGLSTQEPGD VFTYAEFDGI LGMAYPSLAS EYSIPVFDNM
                     Sheep VSNIVDIQQT VGLSTQEPGD VFTYAEFDGI LGMAYPSLAS EYSVPVFDNM
              C._bactrianus VSNIVDPNQT VGLSTEQPGE VFTYSEFDGI LGLAYPSLAS EYSVPVFDNM
         Camelus_dromedarius VSNIVDPNQT VGLSTEQPGE VFTYSEFDGI LGLAYPSLAS EYSVPVFDNM
                       Pig VAGIVDAHQT VGLSTQEPSD IFTYSEFDGI LGLGYPELAS EYTVPVFDNM
                       Rat VSDIVVPHQT VGLSTEEPGD IFTYSPFDGI LGLAYPTFAS KYSVPIFDNM 201                                                                  250
       Bos_bovis_chymosin_B MNRHLVAQDL FSVYMDRNGQ ESMLTLGAID PSYYTGSLHW VPVTVQQYWQ
                     Sheep MDRRLVAQDL FSVYMDRSGQ GSMLTLGAID PSYYTGSLHW VPVTLQKYWQ
              C._bactrianus MDRHLVARDL FSVYMDRNGQ GSMLTLGATD PSYYTGSLHW VPVTVQQYWQ
         Camelus_dromedarius MDRHLVARDL FSVYMDRNGQ GSMLTLGAID PSYYTGSLHW VPVTLQQYWQ
                       Pig MHRHLVAQDL FAVYMSRNDE GSMLTLGAID PSYYTGSLHW VPVTMQLYWQ
                       Rat MNRHLVAQDL FSVYMSRNDQ GSMLTLGAID QSYFIGSLHW VPVTVQGYWQ 251                                                                  300
       Bos_bovis_chymosin_B FTVDSVTISG VVVACEGGCQ AILDTGTSKL VGPSSDILNI QQAIGATQNQ
                     Sheep FTVDSVTISG AVVACEGGCQ AILDTGTSKL VGPSSDILNI QQAIGATQNQ
              C._bactrianus VTVDSVTING VAVACVGGCQ AILDTGTSVL FGPSSDILKI QMAIGATENR
         Camelus_dromedarius FTVDSVTING VAVACVGGCQ AILDTGTSVL FGPSSDILKI QMAIGATENR
                       Pig FTVDSVTING VVVACNGGCQ AILDTGTSML AGPSSDILNI QMAIGATESQ
                       Rat FTVDRITIND EVVACQGGCP AVLDTGTALL TGPGRDILNI QHAIGAVQGQ 301                                                                  350
       Bos_bovis_chymosin_B YGEFDIDCDN LSYMPTVVFE INGKMYPLTP SAYTSQDQGF CTSGFQSENH
                     Sheep YGEFDIDCDS LSSMPTVVFE INGKMYPLTP YAYTSQEEGF CTSGFQGENH
              C._bactrianus YGEFDVNCGS LRSMPTVVFE INGRDFPLAP SAYTSKDQGF CTSGFQGDNN
         Camelus_dromedarius YGEFDVNCGN LRSMPTVVFE INGRDYPLSP SAYTSKDQGF CTSGFQGDNN
                       Pig YGEFDIDCGS LSSMPTVVFE ISGRMYPLPP SAYTNQDQGF CTSGFQGDSK
                       Rat HDQFDIDCWR LNFMPTVVFE INGREFPLPP SAYTNQFQGS CSSGFR..HG 351                        381
       Bos_bovis_chymosin_B SQKWILGDVF IREYYSVFDR ANNLVGLAKA I
                     Sheep SHQWILGDVF IREYYSVFDR ANNLVGLAKA I
              C._bactrianus SELWILGDVF IREYYSVFDR ANNRVGLAKA I
         Camelus_dromedarius SELWILGDVF IREYYSVFDR ANNRVGLAKA I
                       Pig SQHWILGVVF IQEYYSVFDR ANNRVGLAKA I
                       Rat SQMWILGDVF IREFYSVFDR ANNRVGLAKA I
```

VARIANTS OF CHYMOSIN WITH IMPROVED PROPERTIES

CROSS-REFERENCE TO RELATED APPLICATIONS

The present application is the U.S. National Stage of International Application PCT/EP2016/064414, filed Jun. 22, 2016, and claims priority to European Patent Application No, 15173099.1, filed Jun. 22, 2015.

FIELD OF THE INVENTION

The present invention relates to variants of chymosin with improved properties.

BACKGROUND ART

Chymosin (EC 3.4.23.4) and pepsin (EC 3.4.23.1), the milk clotting enzymes of the mammalian stomach, are aspartic proteases belonging to a broad class of peptidases.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, i.e. Bos taurus, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprises 323 aa.

Chymosin is produced naturally in mammalian species such as bovines, camels, caprines, buffaloes, sheep, pigs, humans, monkeys and rats.

Bovine and camel chymosin has for a number of years been commercially available to the dairy industry.

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks κ-casein, resulting in a metastable state of the casein micelle structure and a second phase, where the milk subsequently coagulates and forms a coagulum (reference 1). Besides facilitating coagulation of milk by cleaving κ-casein, chymosins cleave β-casein (β-casein), primarily between Leu192 and Tyr193, resulting in the formation of a β(193-209) peptide. Further proteolysis of β(193-209) and formation of short hydrophobic peptides may result in an undesirable bitter flavor of the product.

WO02/36752A2 (Chr. Hansen) describes recombinant production of camel chymosin.

WO2013/174840A1 (Chr. Hansen) describes mutants/variants of bovine and camel chymosin.

WO2013/164479A2 (DSM) describes mutants of bovine chymosin.

The references listed immediately below may in the present context be seen as references describing mutants of chymosin:

Suzuki et al: Site directed mutagenesis reveals functional contribution of Thr218, Lys220 and Asp304 in chymosin, Protein Engineering, vol. 4, January 1990, pages 69-71;

Suzuki et al: Alteration of catalytic properties of chymosin by site-directed mutagenesis, Protein Engineering, vol. 2, May 1989, pages 563-569;

van den Brink et al: Increased production of chymosin by glycosylation, Journal of biotechnology, vol. 125, September 2006, pages 304-310;

Pitts et al: Expression and characterisation of chymosin pH optima mutants produced in Tricoderma reesei, Journal of biotechnology, vol. 28, March 1993, pages 69-83;

M. G. Williams et al: Mutagenesis, biochemical characterization and X-ray structural analysis of point mutants of bovine chymosin, Protein engineering design and selection, vol. 10, September 1997, pages 991-997;

Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871;

Chitpinityol et al: Site-specific mutations of calf chymosin B which influence milk-clotting activity, Food Chemistry, vol. 62, June 1998, pages 133-139;

Zhang et al: Functional implications of disulfide bond, Cys45-Cys50, in recombinant prochymosin, Biochimica et biophysica acta, vol. 1343, December 1997, pages 278-286.

None of the prior art references mentioned above describe directly and unambiguously any of the chymosin variants with lowered β-casein cleavage frequency at similar clotting activity compared to the parent from which the variant is derived, as described below.

SUMMARY OF THE INVENTION

The problem to be solved by the present invention is to provide variants of chymosin which, when compared to the parent polypeptide, has a lower lowered βcasein cleavage frequency while substantially maintaining its clotting efficiency.

Accordingly, the present invention provides isolated chymosin polypeptide variants characterized in that:

(a) the isolated chymosin polypeptide variant has a specific clotting ac-tivity (IMCU/mg total protein) that is at least 80% of the specific clotting activity of isolated camel chymosin polypeptide characterized by SEQ ID NO:4; and (b) the isolated chymosin polypeptide variant cleaves β-casein with a frequency of less than 50% of the frequency of β-casein cleavage of isolated camel chymosin polypeptide characterized by SEQ ID NO:4, wherein β-casein cleavage is determined by quantifying β-casein peptides obtained by incubating skim milk with the chymosin variant or the camel chymosin, wherein quantification is carried out by RP-HPLC coupled to an ESI-Q-TOF mass spectrometer.

The isolated chymosin polypeptide variant of present invention may be derived from a parent polypeptide has at least 80%, such as at least e.g. 85%, 95%, 97%, 98%, 99%, 100% sequence identity with the polypeptide of SEQ ID NO:4 (camel chymosin).

In a related aspect, the isolated chymosin polypeptide variant of present invention has at least 70%, such as at least e.g. 75%, 80%, 90%, 100%, 110%, 120%, 130% or 150% of the specific clotting activity of isolated camel chymosin polypeptide characterized by SEQ ID NO:4.

In yet a related aspect, the isolated chymosin polypeptide variant of present invention preferably has at least has less than 50%, such as e.g. less than 40%, less than 30%, less than 20%, less than 15%, less than 10% or less than 6% of the unspecific proteolytic activity (P) of isolated camel chymosin polypeptide characterized by SEQ ID NO:4.

In a further related aspect, the isolated chymosin polypeptide variant of present invention has at least has a C/P ratio of at least 300%, 400%, 500%, 600%, 700%, 800%, 1000%, 1200%, 1400% or 1600% of the C/P ratio of isolated camel chymosin polypeptide characterized by SEQ ID NO:4.

The isolated chymosin polypeptide variant of present invention may comprise one or more amino acid substitutions, deletions or insertions, wherein the one or more substitution, deletion or insertion is specified in relation to the amino acid sequence of SEQ ID NO:4: Y11, L130, S132, V32, S226, R266, L12, V221, S255, S277, L222, L253, M157, V260, S271, H76, K19, V183, S164, I263, V51, T239, Y307, R67, G251, R61, Q288, E83, D59, V309, S273, G251, S154, Y21, V203, L180, E294, G289, L215, D144, I303, L105, T284, Y127, V248, K321, V205, E262, K231, R316, M256, D158, D59, N249, L166, R242 or I96, and more specifically such as e.g. Y11I, Y11V, L130I, S132A, V32L, S226T, R266V, L12M, V221M, S255Y, S277N, L222I, L253I, M157L, V260T, S271P, H76Q, K19T, V183I, S164G, I263L, V51L, T239S, Y307F, R67Q, G251D, R61Q, Q288E, E83S, D59N, V309I, S273Y, G251W, S154A, Y21S, V203A, L180I, E294Q, G289S, L215V, D144Q, I303L, L105E, T284S, Y127F, V248I, K321P, V205I, E262T, K231N, R316L, M256L, D158S, D59N, N249E, L166V, R242E and/or I96L.

The present invention further provides methods of making the isolated chymosin polypeptide variants of present invention, methods of making a food or feed product using the isolated chymosin polypeptide variants, food and feed products comprising these variants as well as the use of the variants for making food and feed products.

In a related alternative aspect, the invention relates to methods for making an isolated chymosin polypeptide with decreased comprising the following steps:
  (a): making an alteration at one or more positions in the DNA sequence encoding the polypeptide of SEQ ID NO:4, wherein the alteration comprises a substitution, a deletion or an insertion in at least one amino acid position corresponding to any of positions:
Y11, L130, S132, V32, S226, R266, L12, V221, S255, S277, L222, L253, M157, V260, S271, H76, K19, V183, S164, I263, V51, T239, Y307, R67, G251, R61, Q288, E83, D59, V309, S273, G251, S154, Y21, V203, L180, E294, G289, L215, D144, I303, L105, T284, Y127, V248, K321, V205, E262, K231, R316, M256, D158, D59, N249, L166, R242 or I96 in SEQ ID NO:4;
  (b): producing and isolating the altered polypeptide of step (a).

The isolated chymosin produced by the methods above, may comprise one or more of the following substitutions:
Y11I, Y11V, L130I, S132A, V32L, S226T, R266V, L12M, V221M, S255Y, S277N, L222I, L253I, M157L, V260T, S271P, H76Q, K19T, V183I, S164G, I263L, V51L, T239S, Y307F, R67Q, G251D, R61Q, Q288E, E83S, D59N, V309I, S273Y, G251W, S154A, Y21S, V203A, L180I, E294Q, G289S, L215V, D144Q, I303L, L105E, T284S, Y127F, V248I, K321P, V205I, E262T, K231N, R316L, M256L, D158S, D59N, N249E, L166V, R242E and/or I96L.

In a related aspect the isolated chymosin polypeptide variant of present invention and the variant produced by the methods above may comprise a combination of substitutions and wherein each substitution is specified in relation to the amino acid sequence of SEQ ID NO:4:
I96+G163+V221; R67+H76+S132+V248+S271; R67+L130+M157;
V136+V221+L222+S226; S132+R254+V259+Y307; V32+I96+S277;
L130+M142+I200+V259+E294; L130+S132+V32;
L130+G163+Y307; R61+L166+T239; L130+T239+S277+L295;
D98+H146+V203+I263+S271; S132+V221+S255+S273+V317;
H76+L222+G251; H76+K231+G244;
Y127+S132+D158; V221+V248+L253+L295; V32+R61+H146;
V32+E294+R316+V317; H76+I96+D158; D98+M157+V183;
S226+G244+I263+G289; G70+L130+Y268; D59+V248+L222+V248;
R67+G70+H146+Q188+S226; 574+H76+M142+M157+G163;
R61+S226+T239+V248+G251; V32+L130+R145+L222+D279;
D59+L222+G251+E83+Q162; D59+L222+G251+F17+Y21;
D59+L222+G251+H76+S164; D59+L222+G251+K62+M165; D59+L222+G251+Q162+V155; D59+L222+G251+S273+L166; D59+L222+G251+Y268+V198; D59+L222+G251+S273+F66; D59+L222+G251+M165+L166; D59+L222+G251+H76+M165; D59+L222+G251+F17+S273;
D59+L222+G251+L166+I45;
D59+L222+G251+L180+T284; D59+L222+G251+V32+L12+T284;
D59+L222+G251+Y21+L166; D59+L222+G251+V155+E262+V32;
D59+L222+G251+L105+S164; D59+L222+G251+Y21+L215+L105;
D59+L222+G251+I96+T177+K321; D59+L222+G251+F17+T284+V203;
D59+L222+G251+V32+K321+V260; D59+L222+G251+V198+V32+E83;
D59+L222+G251+I96+V203+V309; D59+L222+G251+Y268+L215+V32;
D59+L222+G251+H76+L105+V260; D59+L222+G251+Y21+H76+Y268;
D59+L222+G251+S164+R266+I96; D59+L222+G251+H181+F66+V32;
D59+L222+G251+H181+R266+D267; D59+L222+G251+Y268+L12+D267;
D59+L222+G251+L166+E262+T177; D59+L222+G251+F66+Q288+I96;
D59+L222+G251+V203+R266+F223; D59+L222+G251+I303+S154+V260;
D59+L222+G251+Y21+T284+I96; D59+L222+G251+Q288+K19+T177;
D59+L222+G251+K62+Y268+K19;
L12+Y21+D59+H76+M165+V198+L222+G251+Q288;
L12+Y21+D59+H76+M165+L222+G251+S273;
L12+D59+H76+M165+V198+L222+G251+S273+K321;
L12+D59+H76+S154+M165+V203+L222+G251+V309;
L12+D59+H76Q+D98+L222;
L12+K19+V32+D59+H76+D144+M165+L222+G251;
L12+Y21+D59+H76+M165+V203+L222+G251+E262;
L12+V51+H76+M165+G251;
L12+D59+F66+H76+M165+L180+L222+G251+V309;
L12+D59+H76+S154+M165+L222+G251+Q288;
L12+D59+H76+D98+M165+L222+G251+E262+Q288;

L12+V51+D59+H76+L166+L222+G251;
L12+D59+H76+D144+M165+V203+L222;
L12+D59+144+M165+L166+L222+G251;
L12+K19+D59+H76+S154+M165+V198+L222+G251;
L12+H76+D98+M165+L222+G251;
L12+V32+D59+H76+M165+L180+V198+L222+G251;
L12+D59+H76+S154+M165+S273;
L12+V51+D59+F66Y+H76Q+M165E+V203A+L222I+G251W;
L12+V32+H76+M165+L222+E262; L12+N50+D59+H76+M165+G251+E262; V51+D59+H76+M165+L180+L222+G251+E262; L12+D59+H76+M165+G251+Q288+V309+K321; L12+N50+D59+V203+L222+G251; L12+D59+H76+L180+L222+G251+K321; L12+Y21+D59+M165+L222+K321; D59+H76+M165+L166+V198+L222; L12+K19+N50+D59+H76+M165+L222+Q288; L12+Y21+N50+D59+F66+H76+D144+M165+L222+G251; H76+S132+S164+L222+N249+G251; Y21+D59+H76+S164+L166+N249+G251+S273; D59+H76+S164+L222+R242+S273+V309; D59+H76+L130+L166+L222+N249+G251+S273; Y21+D59+S164+L222+R242+G251+S273+V309; K19+Y21+D59+H76+S132+S164+L222+G251+S273; D59+H76+I96+L130+S164+L222+R242+G251; H76+S164+L166+L222+S226+S273; K19+D59+I96+S164+L222+G251; Y21+H76+S164+L222+R242+G251+S273; H76+I96+S164+L222+R242+G251+S273; H76+S164+L222+N249+G251+S273+V309; K19+D59+H76+S164+L222+N249+S273; Y21+D59+H76+S164+L222+S226+G251+S273+V309; H76+S164+L166+L222+R242+G251+S273; D59+H76+I96+S164+L222+S226+N249+G251+S273; D59+H76+L130+S164+L166+L222+G251+S273+V309; D59+S132+S164+L222+R242+N249+G251+S273; H76+I96+S164+G251+S273+V309; D59+H76+L130+S164+G251+V309; K19+D59+S164+L166+L222+S226+G251+S273; D59+H76+I96+S132+S164+L222+S226+G251+S273; K19+D59+H76+I96+S164+L166+L222+G251+S273; K19+D59+H76+L130+S164+L222+S226+G251+S273; K19+D59+H76+S132+L222+G251+S273+V309; H76+L130+L222+S226+G251+S273; K19+Y21+D59+H76+L130+S164+L222+S273; Y21+D59+H76+I96+S164+L222+N249+G251+S273; K19+D59+H76+S164+R242+N249+G251+S273; D59+H76+S164+L222+S226+R242; D59+H76+I96+S132+S164+L166+L222+G251+S273; D59+H76+S132+S164+L166+S273; Y21+D59+S164+L222+S226+N249+G251+S273; D59+H76+L130+S132+S164+L222+R242+G251+S273; D59+H76+S164+L166+L222+N249+G251+S273+V309; D59+H76+I96+S164+L222+S226+G251+S273+V309; K19+D59+H76+L166+L222+R242+G251+S273; Y21+D59+H76+I96+L222+S273; D59+H76+I96+L130+S164+L222+N249+G251+S273; L130+S164+L222+S273; K19+Y21+H76+S164+L222+G251+S273; Y21+D59+H76+L130+S132+S164+L222+G251+S273; D59+H76+S226+R242+G251+S273; K19+D59+I96+S164+L222+G251; Y11+K19+D59+I96+L222+R242+G251; K19+D59+I96+S164+G251; K19+I96+S164+L166+L222+R242; K19+D59+I96+S164+L166+L222+R242+G251+L253; D59+196+S164+L222+R242+L253+I263; K19+D59+E83+196+L222+G251+I263; Y11+K19+D59+S164+L222+G251+I263; K19+D59+I96+S164+L166+G251+L253; K19+I96+S164+L222+N249+G251+L253; K19+I96+L222+R242+L253; K19+E83+I96+S164+L222+R242+G251+L253; D59+E83+I96+S164+L222+G251; K19+D59+I96+S164+L222+R242+N249+G251; K19+I96+S164+L166+L222+N249+I263; D59+I96+L166+L222+R242+G251; K19+D59+E83+S164+L166+L222+R242+G251; Y11+K19+D59+E83+I96+S164+L222+N249; K19+E83+I96+S164+L222+R242+L253; K19+D59+I96+S164+L166+L222+R242+N249; Y11+K19+D59+I96+S164+L166+L222+R242+G251+L253; K19+I96+S164+L222+R242+I263; Y11+D59+I96+S164+L222+G251+L253; K19+D59+196+S164+L166+L222+R242+I263; Y11+K19+D59+I96+S164+L166+L222+G251; K19+196+S164+L166+L222+R242+N249+G251+I263; K19+I96+S164+R242+L253; K19+D59+E83+I96+S164+L222+G251; K19+D59+I96+S164+L222+N249+G251+I263; K19+D59+I96+S164+L222+N249+G251+L253+I263; Y11+K19+I96+S164+L222+R242+G251; I96+S164+L222+R242+N249+G251+1263; K19+D59+196+S164+L166+L222+R242+G251+1263; K19+D59+I96+S164+L222+R242+N249+L253; H76+I96+S164+L222+R242+G251+S273; K19+E83+I96+S164+L222+R242+N249+G251+L253; I96+S164+L166+L222+R242+N249+1263; Y11+K19+E83+I96+S164+L166+L222+R242+G251; Y11+K19+I96+S164+L166+L222+R242; Y11+E83+I96+S164+L222+R242+G251+L253+I263; Y11+I96+S164+L222+R242+N249+L253+1263; K19+196+S164+L166+L222+R242+N249+I263; Y11+E83+I96+S164+L222+R242+L253+I263; K19+E83+I96+S164+L166+L222+R242+N249+G251+L253; I96+S164+L222+R242+G251+S274; H76+I96+S164+L222+R242+G251; I96+S164+L222+R242+G251; V32+N100+N291; V221+N100+N291; D290+N100+N291; V136+N100+N291; E240+N100+N291; R242+N100+N291; G289+N100+N291; N292+N100+N291; L295+N100+N291; V136+N100+N291; D290+N100+N291; F119+N100+N291; Q280+N100+N291; F282+N100+N291; R254+N100+N291; R242+N100+N291; V203+N100+N291; N249+N100+N291; H56+N100+N291; 574+N100+N291; A131+N100+N291; Y190+N100+N291; I297+N100+N291; H76+N100+N291; S273+N100+N291; K19+N100+N291; D59+N100+N291; L222+N100+N291; V309+N100+N291; I96+N100+N291; Y21+N100+N291; L130+N100+N291; S132+N100+N291; S226+N100+N291; G251+N100+N291; Y243+N100+N291; S273+N100+N291; R242+Q280+N100+N291; R242+N252+N100+N291; N252+Q280+N100+N291; Y243+Q280+N100+N291; Y243+N252+N100+N291;

R254+Q280+N100+N291; S273+Q280+N100+N291;
R242+G251+N100+N291; R242+G251+Q280+N100+N291;
R242+S273+Q280+N100+N291; N252+S273+Q280+N100+N291;
G251+S273+Q280+N100+N291; R242+R254+Q280+N100+N291;
R242+R254+S273+Q280+N100+N291; Y243+R254+S273+N100+N291;
V223+N252+N291; E290+N252+N291; A117+N252+N291; I136+N252+N291;
Q242+N252+N291; Q278+N252+N291; S289+N252+N291;
Q294+N252+N291; D249+N252+N291; D251+N252+N291;
G244+N252+N291; Q56+N252+N291; L32+N252+N291; K71+N252+N291;
P72+N252+N291; Q83+N252+N291; V113+N252+N291; E133+N252+N291;
Y134+N252+N291; K71+N252+N291; Y11+N100+N291;
Y11+D290+N100+N291; L12+N100+N291; D13+N100+N291;
D13+N100+N291; R67+N100+L130+M157+V248+N291;
N100+L130+S132+M157+K231; R67+I96+L130+M157+L222+M256;
R67+L130+S132+M157+R242+V248; R67+N100+M157+R242+M256;
R67+G70+M157+R242+V248; V32+R67+M157+L222+R242;
Y11+R67+M157+V248+M256; R67+V136+M157+L222+V248;
L130+M157+V248+M256+N291; R67+I96+L130+M157+K231+R242;
V32+R67+L130+M157+L222+K231; L130+V136+M157+L222+N292;
R67+G70+M157+L222+N291; V32+R67+L130+K231+N292;
Y11+R67+N100+L130+V136+M157; R67+L130+L222+R242+M256;
R67+M157+L222+V248+N292; V32+R67+M157+M256+N291;
R67+L130+S132+M157+L222+N292; R67+N100+L130+M157+K231+N291;
R67+L130+K231+V248+N291; Y11+R67+L130+M157+L222+K231;
I45+L130+M157+K231+R242; V32+R67+V136+M157+N291;
R67+N100+L130+D158+V248; I45+R67+L130+M157+L222+K231;
V32+R67+L130+S132+M157+V248; Y11+R67+L130+M157+N291+N292;
R67+N100+L130+M157+L222+K231; I45+R67+G70+L130+S132;
I45+R67+L130+V248+N292; Y11+R67+L130+M157+L222+R242;
R67+N100+D158+L130+M157+L222; R67+L130+V136+M157+K231+V248;
I45+R67+L130+L222+N291; R67+G70+L130+M157+K231+M256;
V32+R67+L130+M157+D158+V248; R67+L130+M157+D158+R242+N291;
R67+L130+M157+D158+K231+N292; R67+L130+V248+M256+N292;
V32+R67+I96+L130+V248; R67+I96+N100+L130+M157+N292;
V32+R67+G70+N100+M157; V32+R67+L130+M157+K231+M256;
R67+I96+M157+L222+K231; R67+M157+L222+K231+V248;
R67+L130+M157+R242+M256+N292; R67+L222+K231+V248;
R67+S132+L222+K231+R242+V248;
Y11+K19+D59+S164+L166+L222+R242+N249+G251;
Y11+K19+D59+I96+S164+L166+L222+R242+N249+G251;
Y11+K19+D59+I96+S164+L166+L222+R242+N249+G251;
Y11+K19+D59+I96+S164+L166+L222+R242+G251;
Y11+K19+D59+I96+L166+L222+R242+N249+G251+L253;
Y11+K19+D59+I96+S164+L166+R242;
Y11+K19+D59+I96+S164+L222+R242+G251;
Y11+K19+D59+I96+S164+L166+R242+N249+G251+L253;
Y11+K19+D59+I96+S164+L166+L222+R242+N249+G251;
Y11+K19+D59+I96+S164+L166+L222+R242+N249+G251+L253;
Y11+K19+D59+L166+L222+R242+N249+G251+L253;
Y11+K19+D59+I96+S164+L166+L222+R242+N249;
Y11+K19+D59+S164+L166+L222+R242+G251;
Y11+K19+D59+I96+S164+R242+G251;
Y11+D59+I96+S164+L166+L222+R242+G251+L253;
Y11+D59+I96+S164+L166+L222+R242+G251;
Y11+D59+I96+S164+L166+L222+R242+G251+L253;
Y11+K19+D59+I96+S164+L222+R242+N249+G251;
Y11+K19+D59+I96+S164+L166+L222+R242+G251;
Y11+K19+D59+I96+S164+L166+L222+R242+N249+L253;
Y11+K19+D59+I96+S164+L166+L222+R242+N249+G251;
Y11+K19+I96+S164+L166+R242+N249+G251;
Y11+K19+D59+I96+S164+L166+L222+R242+G251;
Y11+K19+D59+I96+S164+L222+R242+N249+G251;
Y11+K19+L222+R242+N249+G251; Y11+K19+I96+L222+R242+N249+G251;
Y11+K19+D59+I96+S164+L166+L222+R242+N249+G251;
Y11+K19+I96+S164+L166+L222+R242+N249+G251;
Y11+K19+D59+I96+S164+L166+L222+R242+N249+G251;
Y11+I96+S164+L166+L222+R242+N249+G251;
Y11+K19+D59+I96+S164+L222+R242+N249;
Y11+K19+D59+I96+L222+R242+N249+G251;
Y11+K19+D59+I96+S164+L222+R242;
Y11+K19+D59+I96+S164+L166+R242+G251;
Y11+K19+D59+S164+L166+L222+R242+G251;
Y11+I96+L222+R242+N249+G251; Y11+I96+S164+L222+R242;
Y11+K19+I96+L166+L222+R242+G251;
Y11+D59+I96+S164+L222+R242+G251;
Y11+D59+I96+S164+L222+R242+N249+G251;
Y11+K19+D59+I96+S164+L222+R242+N249+G251;
Y11+D59+I96+S164+L166+L222+R242+G251;
Y11+K19+D59+I96+L222+R242+G251;
Y11+K19+S164+L166+L222+R242+N249+G251;
Y11+D59+I96+S164+L166+L222+R242+N249+G251,
such as e.g.:
I96L+G163E+V221M;
R67Q+H76Q+S132A+V248I+S271P;
R67Q+L130I+M157L;
V136I+V221M+L222I+S226T;
S132A+R254S+V259I+Y307F;
V32L+I96L+S277N;

L130I+M142I+I200V+V259I+E294Q;
L130I+G163E+Y307F;
R61S+L166V+T239S;
L130I+T239S+S277N+L295K;
L130I+S132A+V32L;
D98V+H146R+V203A+I263L+S271P;
S132A+V221M+S255Y+S273Y+V317L;
H76Q+L222I+G251W;
H76Q+K231N+G244D;
Y127F+S132A+D158S;
V221M+V248I+L253I+L295K;
V32L+R61Q+H146R;
V32L+E294Q+R316L+V317L;
H76Q+I96L+D158S;
D98V+M157L+V183I;
S226T+G244D+I263L+G289S;
G70D+L130I+Y268F;
D59N+V248I+L222I+V248I;
R67Q+G70N+H146R+Q188E+S226T;
S74F+H76Q+M142I+M157L+G163E;
R61Q+S226T+T239S+V248I+G251W;
V32L+L130I+R145Q+L222I+D279E;
D59N+L222I+G251D+E83S+Q162S;
D59N+L222I+G251W+F17Y+Y21S;
D59N+L222I+G251D+H76Q+S164G;
D59N+L222I+G251D+K62Q+M165E;
D59N+L222I+G251D+Q162S+V155F;
D59N+L222I+G251D+S273Y+L166V;
D59N+L222I+G251D+Y268F+V198I;
D59N+L222I+G251D+S273Y+F66Y;
D59N+L222I+G251D+M165E+L166V;
D59N+L222I+G251D+H76Q+M165E;
D59N+L222I+G251D+F17Y+S273Y;
D59N+L222I+G251D+L166V+145V;
D59N+L222I+G251W+L180I+T284S;
D59N+L222I+G251D+V32L+L12M+T284S;
D59N+L222I+G251D+Y21S+L166V;
D59N+L222I+G251D+V155F+E262T+V32L;
D59N+L222I+G251D+L105E+S164G;
D59N+L222I+G251D+Y21S+L215V+L105E;
D59N+L222I+G251D+196L+T177S+K321P;
D59N+L222I+G251D+F17Y+T284S+V203A;
D59N+L222I+G251D+V32L+K321P+V260T;
D59N+L222I+G251D+V198I+V32L+E83S;
D59N+L222I+G251D+196L+V203A+V309I;
D59N+L222I+G251D+Y268F+L215V+V32L;
D59N+L222I+G251D+H76Q+L105E+V260T;
D59N+L222I+G251D+Y21S+H76Q+Y268F;
D59N+L222I+G251D+S164G+R266V+196L;
D59N+L222I+G251D+H181N+F66Y+V32L;
D59N+L222I+G251D+H181N+R2661+D267Q;
D59N+L222I+G251D+Y268F+L12M+D267Q;
D59N+L222I+G251D+L166V+E262T+T177S;
D59N+L222I+G251D+F66Y+Q288E+196L;
D59N+L222I+G251D+V203A+R266V+F223A;
D59N+L222I+G251D+1303L+S154A+V260T;
D59N+L222I+G251D+Y21S+T284S+196L;
D59N+L222I+G251D+Q288E+K19T+T177S;
D59N+L222I+G251D+K62Q+Y268F+K19T
L12M+Y21S+D59N+H76Q+M165E+V198I+L222I+G251D+Q288E;
L12M+Y21S+D59N+H76Q+M165E+L222I+G251W+S273Y;
L12M+D59N+H76Q+M165E+V198I+L222I+G251D+S273Y+K321P;
L12M+D59N+H76Q+S154A+M165E+V203A+L222I+G251D+V309I;
L12M+D59N+H76Q+D98V+L222I;
L12M+K19T+V32L+D59N+H76Q+D144Q+M165E+L222I+G251D;
L12M+Y21S+D59N+H76Q+M165E+V203A+L222I+G251D+E262T;
L12M+V51L+H76Q+M165E+G251D;
L12M+D59N+F66Y+H76Q+M165E+L180I+L222I+G251D+V309I;
L12M+D59N+H76Q+S154A+M165E+L222I+G251W+Q288E;
L12M+D59N+H76Q+D98V+M165E+L222I+G251D+E262T+Q288E;
L12M+V51L+D59N+H76Q+L166V+L222I+G251D;
L12M+D59N+H76Q+D144Q+M165E+V203A+L222I;
L12M+D59N+144Q+M165E+L166V+L222I+G251D;
L12M+K19T+D59N+H76Q+S154A+M165E+V198I+L222I+G251D;
L12M+H76Q+D98V+M165E+L222I+G251W;
L12M+V32L+D59N+H76Q+M165E+L180I+V198I+L222I+G251D;
L12M+D59N+H76Q+S154A+M165E+S273Y;
L12M+V51L+D59N+F66Y+H76Q+M165E+V203A+L222I+G251W;
L12M+V32L+H76Q+M165E+L222I+E262T;
L12M+N50D+D59N+H76Q+M165E+G251W+E262T;
V51L+D59N+H76Q+M165E+L180I+L222I+G251D+E262T;
L12M+D59N+H76Q+M165E+G251D+Q288E+V309I+K321P;
L12M+N50D+D59N+V203A+L222I+G251D;
L12M+D59N+H76Q+L180I+L222I+G251W+K321P;
L12M+Y21S+D59N+M165E+L222I+K321P;
D59N+H76Q+M165E+L166V+V198I+L222I;
L12M+K19T+N50D+D59N+H76Q+M165E+L222I+Q288E;
L12M+Y21S+N50D+D59N+F66Y+H76Q+D144Q+M165E+L222I+G251D;
H76Q+S132A+S164G+L222I+N249D+G251D;
Y21S+D59N+H76Q+S164G+L166V+N249D+G251D+S273Y;
D59N+H76Q+S164G+L222I+R242E+S273Y+V309I;
D59N+H76Q+L130I+L166V+L222I+N249D+G251D+S273Y;
Y21S+D59N+S164G+L222I+R242E+G251D+S273Y+V309I;
K19T+Y21S+D59N+H76Q+S132A+S164G+L222I+G251D+S273Y;
D59N+H76Q+196L+L130I+S164G+L222I+R242E+G251D;
H76Q+S164G+L166V+L222I+S226T+S273Y;
K19T+D59N+I96L+S164G+L222I+G251D;
Y21S+H76Q+S164G+L222I+R242E+G251D+S273Y;
H76Q+196L+S164G+L222I+R242E+G251D+S273Y;
H76Q+S164G+L222I+N249D+G251D+S273Y+V309I;
K19T+D59N+H76Q+S164G+L222I+N249D+S273Y;
Y21S+D59N+H76Q+S164G+L222I+S226T+G251D+S273Y+V309I;
H76Q+S164G+L166V+L222I+R242E+G251D+S273Y;
D59N+H76Q+196L+S164G+L222I+S226T+N249D+G251D+S273Y;
D59N+H76Q+L130I+S164G+L166V+L222I+G251D+S273Y+V309I;
D59N+S132A+S164G+L222I+R242E+N249D+G251D+S273Y;
H76Q+196L+S164G+G251D+S273Y+V309I;
D59N+H76Q+L130I+S164G+G251D+V309I;

K19T+D59N+S164G+L166V+L222I+S226T+G251D+S273Y;
D59N+H76Q+I96L+S132A+S164G+L222I+S226T+G251D+S273Y;
K19T+D59N+H76Q+I96L+S164G+L166V+L222I+G251D+S273Y;
K19T+D59N+H76Q+L130I+S164G+L222I+S226T+G251D+S273Y;
K19T+D59N+H76Q+S132A+L222I+G251D+S273Y+V309I;
H76Q+L130I+L222I+S226T+G251D+S273Y;
K19T+Y21S+D59N+H76Q+L130I+S164G+L222I+S273Y;
Y21S+D59N+H76Q+I96L+S164G+L222I+N249D+G251D+S273Y;
K19T+D59N+H76Q+S164G+R242E+N249D+G251D+S273Y;
D59N+H76Q+S164G+L222I+S226T+R242E;
D59N+H76Q+I96L+S132A+S164G+L166V+L222I+G251D+S273Y;
D59N+H76Q+S132A+S164G+L166V+S273Y;
Y21S+D59N+S164G+L222I+S226T+N249D+G251D+S273Y;
D59N+H76Q+L130I+S132A+S164G+L222I+R242E+G251D+S273Y;
D59N+H76Q+S164G+L166V+L222I+N249D+G251D+S273Y+V309I;
D59N+H76Q+196L+S164G+L222I+S226T+G251D+S273Y+V309I;
K19T+D59N+G251D+S273; H76Q+L166V+L222I+R242E+G251D+S273Y;
Y21S+D59N+H76Q+196L+L222I+S273Y;
D59N+H76Q+I96L+L130I+S164G+L222I+N249D+G251D+S273Y;
L130I+S164G+L222I+S273Y;
K19T+Y21S+H76Q+S164G+L222I+G251D+S273Y;
Y21S+D59N+H76Q+L130I+S132A+S164G+L222I+G251D+S273Y;
D59N+H76Q+S226T+R242E+G251D+S273Y;
K19T+D59N+I96L+S164G+L222I+G251D;
Y11I+K19T+D59N+196V+L222I+R242D+G251D;
K19S+D59N+I96V+S164G+G251D; K19S+I96L+S164G+L166V+L222I+R242E;
K19T+D59N+I96L+S164G+L166V+L222I+R242D+G251D+L253I;
D59N+I96L+S164G+L222I+R242E+L253I+I263L;
K19T+D59N+E83T+I96L+L222I+G251D+I263L;
Y11I+K19T+D59N+S164G+L222I+G251D+I263V;
K19T+D59N+I96L+S164G+L166I+G251D+L253V;
K19T+196V+S164G+L222I+N249D+G251D+L253I;
K19T+196L+L222I+R242E+L253I;
K19T+E83S+196L+S164G+L222I+R242E+G251D+L253I;
D59N+E83T+I96L+S164N+L222V+G251D;
K19S+D59N+I96L+S164G+L222I+R242E+N249E+G251D;
K19T+I96L+S164G+L166V+L222I+N249D+I263L;
D59N+I96L+L166V+L222I+R242E+G251D;
K19T+D59N+E83T+S164G+L166V+L222I+R242D+G251D;
Y11I+K19T+D59N+E83S+I96L+S164G+L222I+N249D;
K19T+E83T+I96L+S164G+L222I+R242E+L253V;
K19T+D59N+I96L+S164G+L166I+L222I+R242E+N249D;
Y11V+K19T+D59N+I96L+S164G+L166V+L222I+R242E+G251D+L253I;
K19T+I96L+S164N+L222I+R242E+I263L;
Y11V+D59N+I96L+S164G+L222I+G251D+L253V;
K19T+D59N+I96V+S164G+L166V+L222I+R242E+I263L;
Y11V+K19T+D59N+I96L+S164N+L166I+L222I+G251D;
K19T+I96L+S164G+L166V+L222I+R242E+N249D+G251D+I263V;
K19T+I96L+S164G+R242E+L253I;
K19S+D59N+E83S+I96L+S164N+L222I+G251D;
K19T+D59N+I96L+S164G+L222V+N249E+G251D+I263V;
K19T+D59N+I96L+S164G+L222I+N249E+G251D+L253V+I263L;
Y11I+K19T+I96L+S164G+L222V+R242E+G251D;
I96L+S164G+L222I+R242E+N249D+G251D+I263L;
K19T+D59N+I96L+S164G+L166I+L222I+R242D+G251D+I263V;
K19T+D59N+I96L+S164G+L222V+R242E+N249D+L253I;
H76Q+I96L+S164G+L222I+R242E+G251D+S273Y;
K19T+E83S+I96L+S164G+L222I+R242E+N249D+G251D+L253I;
I96L+S164G+L166V+L222I+R242E+N249D+I263L;
Y11V+K19T+E83S+I96L+S164G+L166V+L222I+R242E+G251D;
Y11V+K19T+I96L+S164G+L166V+L222I+R242E;
Y11V+E83S+I96L+S164G+L222I+R242E+G251D+L253I+I263L;
Y11V+I96L+S164G+L222I+R242E+N249D+L253I+I263L;
K19T+I96L+S164G+L166V+L222I+R242E+N249D+I263L;
Y11V+E83S+I96L+S164G+L222I+R242E+L253I+I263L;
K19T+E83S+I96L+S164G+L166V+L222I+R242E+N249D+G251D+L253I;
I96L+S164G+L222I+R242E+G251D+S274Y;
H76Q+I96L+S164G+L222I+R242E+G251D;
I96L+S164G+L222I+R242E+G251D; V32L+N100Q+N291Q;
V221K+N100Q+N291Q; D290E+N100Q+N291Q; V136I+N100Q+N291Q;
E240Q+N100Q+N291Q; R242Q+N100Q+N291Q; G289S+N100Q+N291Q;
N292H+N100Q+N291Q; L295K+N100Q+N291Q; V136E+N100Q+N291Q;
D290L+N100Q+N291Q; F119Y+N100Q+N291Q; Q280E+N100Q+N291Q;
F282E+N100Q+N291Q; R254S+N100Q+N291Q; R242E+N100Q+N291Q;
V203R+N100Q+N291Q; N249R+N100Q+N291Q; H56K+N100Q+N291Q;
S74D+N100Q+N219Q; A131D+N100Q+N291Q; Y190A+N100Q+N291Q;
I297A+N100Q+N291Q; H76Q+N100Q+N291Q; S273Y+N100Q+N291Q;
K19T+N100Q+N291Q; D59N+N100Q+N291Q; L222I+N100Q+N291Q;
V309I+N100Q+N291Q; I96L+N100Q+N291Q; Y21S+N100Q+N291Q;
L130I+N100Q+N291Q; S132A+N100Q+N291Q; S226T+N100Q+N291Q;
G251D+N100Q+N291Q; Y243E+N100Q+N291Q; S273D+N100Q+N291Q;
R242E+Q280E+N100Q+N291Q; R242E+N252D+N100Q+N291Q;
N252D+Q280E+N100Q+N291Q; Y243E+Q280E+N100Q+N291Q;
Y243E+N252D+N100Q+N291Q; R254E+Q280E+N100Q+N291Q;

S273D+Q280E+N100Q+N291Q; R242E+G251D+N100Q+N291Q;
R242E+G251D+Q280E+N100Q+N291Q;
R242E+S273D+Q280E+N100Q+N291Q;
N252D+S273D+Q280E+N100Q+N291Q;
G251D+S273D+Q280E+N100Q+N291Q;
R242E+R254E+Q280E+N100Q+N291Q;
R242E+R254E+S273D+Q280E+N100Q+N291Q;
Y243E+R254E+S273D+N100Q+N291Q; V223F+N252Q+N291Q;
E290D+N252Q+N291Q; A117S+N252Q+N291Q; I136V+N252Q+N291Q;
Q242R+N252Q+N291Q; Q278K+N252Q+N291Q; S289G+N252Q+N291Q;
Q294E+N252Q+N291Q; D249N+N252Q+N291Q; D251G+N252Q+N291Q;
G244D+N252Q+N291Q; Q56H+N252Q+N291Q; L32I+N252Q+N291Q;
K71E+N252Q+N291Q; P72T+N252Q+N291Q; Q83T+N252Q+N291Q;
V113F+N252Q+N291Q; E133S+N252Q+N291Q; Y134G+N252Q+N291Q;
K71A+N252Q+N291Q; Y11H+N100Q+N291Q; Y11K+N100Q+N291Q;
Y11R+N100Q+N291Q; Y11H+D290E+N100Q+N291Q;
Y11R+D290E+N100Q+N291Q; Y11F+N100Q+N291Q; Y11I+N100Q+N291Q;
Y11L+N100Q+N291Q; L12F+N100Q+N291Q; L12I+N100Q+N291Q;
D13N+N100Q+N291Q; D13Q+N100Q+N291Q; D13S+N100Q+N291Q;
D13T+N100Q+N291Q; D13F+N100Q+N291Q; D13L+N100Q+N291Q;
D13V+N100Q+N291Q; D13Y+N100Q+N291Q
R67Q+N100Q+L130I+M157L+V248I+N291Q;
N100Q+L130I+S132A+M157L+K231N;
R67Q+I96L+L130I+M157L+L222I+M256L;
R67Q+L130I+S132A+M157L+R242E+V248I;
R67Q+N100Q+M157L+R242E+M256L; R67Q+G70D+M157L+R242E+V248I;
V32L+R67Q+M157L+L222I+R242E; Y11V+R67Q+M157L+V248I+M256L;
R67Q+V136I+M157L+L222I+V248I; L130I+M157L+V248I+M256L+N291Q;
R67Q+I96L+L130I+M157L+K231N+R242E;
V32L+R67Q+L130I+M157L+L222I+K231N;
L130I+V136I+M157L+L222I+N292H; R67Q+G70D+M157L+L222I+N291Q;
V32L+R67Q+L130I+K231N+N292H; Y11V+R67Q+N100Q+L130I+V136I+M157L; R67Q+L130I+L222I+R242E+M256L; R67Q+M157L+L222I+V248I+N292H; V32L+R67Q+M157L+M256L+N291Q; R67Q+L130I+S132A+M157L+L222I+N292H; R67Q+N100Q+L130I+M157L+K231N+N291Q; R67Q+L130I+K231N+V248I+N291Q; Y11V+R67Q+L130I+M157L+L222I+K231N; I145V+L130I+M157L+K231N+R242E; V32L+R67Q+V136I+M157L+N291Q; R67Q+N100Q+L130I+D158S+V248I; I45V+R67Q+L130I+M157L+L222I+K231N; V32L+R67Q+L130I+S132A+M157L+V248I; Y11V+R67Q+L130I+M157L+N291Q+N292H; R67Q+N100Q+L130I+M157L+L222I+K231N; I45V+R67Q+G70D+L130I+S132A; I45V+R67Q+L130I+V248I+N292H; Y11V+R67Q+L130I+M157L+L222I+R242E; R67Q+N100Q+D158S+L130I+M157L+L222I; R67Q+L130I+V136I+M157L+K231N+V248I; I45V+R67Q+L130I+L222I+N291Q; R67Q+G70D+L130I+M157L+K231N+M256L; V32L+R67Q+L130I+M157L+D158S+V248I; R67Q+L130I+M157L+D158S+R242E+N291Q; R67Q+L130I+M157L+D158S+K231N+N292H; R67Q+L130I+V248I+M256L+N292H; V32L+R67Q+I96L+L130I+M157L+V248I; R67Q+I96L+N100Q+L130I+M157L+N292H; V32L+R67Q+G70D+N100Q+M157L; V32L+R67Q+L130I+M157L+K231N+M256L; R67Q+I96L+M157L+L222I+K231N; R67Q+M157L+L222I+K231N+V248I; R67Q+L130I+M157L+R242E+M256L+N292H; R67Q+L222I+K231N+V248I; R67Q+S132A+L222I+K231N+R242E+V248I; Y11V+K19T+D59N+S164G+L166V+L222I+R242E+N249E+G251D; Y11V+K19T+D59N+I96L+S164G+L166I+L222I+R242E+N249E+G251D; Y11I+K19T+D59N+I96L+S164G+L166V+L222I+R242E+N249E+G251D; Y11I+K19T+D59N+I96L+S164G+L166I+L222I+R242E+G251D; Y11V+K19T+D59N+I96L+L166V+L222V+R242E+N249E+G251D+L253I; Y11V+K19T+D59N+I96L+S164G+L166V+R242E; Y11V+K19T+D59N+I96L+S164G+L222V+R242E+G251D; Y11V+K19T+D59N+I96L+S164G+L166I+R242E+N249E+G251D+L253I; Y11V+K19T+D59N+I96L+S164G+L166V+L222V+R242E+N249E+G251D; Y11V+K19T+D59N+I96L+S164G+L166I+L222V+R242E+N249E+G251D+L253I; Y11V+K19T+D59N+L166V+L222I+R242E+N249E+G251D+L253I; Y11V+K19T+D59N+I96L+S164G+L166V+L222I+R242E+N249E; Y11V+K19T+D59N+S164G+L166I+L222I+R242E+G251D; Y11V+K19T+D59N+I96L+S164G+R242E+G251D; Y11V+D59N+I96L+S164G+L166I+L222V+R242E+G251D+L253I; Y11V+D59N+I96L+S164G+L166I+L222I+R242E+G251D; Y11I+D59N+I96L+S164G+L166V+L222I+R242E+G251D+L253I; Y11V+K19T+D59N+I96L+S164G+L222I+R242E+N249E+G251D; Y11V+K19T+D59N+I96L+S164G+L166I+L222V+R242E+G251D; Y11V+K19T+D59N+I96L+S164G+L166V+L222V+R242E+N249E+L253I; Y11V+K19T+D59N+I96L+S164G+L166I+L222V+R242E+N249E+G251D; Y11I+K19T+I96L+S164G+L166V+R242E+N249E+G251D; Y11V+K19T+D59N+I96L+S164G+L166V+L222V+R242E+G251D; Y11V+K19T+D59N+I96L+S164G+L222V+R242E+N249E+G251D; Y11I+K19T+L222V+R242E+N249E+G251D; Y11V+K19T+I96L+L222V+R242E+N249E+G251D; Y11I+K19T+D59N+I96L+S164G+L166V+L222V+R242E+N249E+G251D;

Y11V+K19T+I96L+S164G+L166V+L222V+R242E+ N249E+G251D;
Y11I+K19T+D59N+I96L+S164G+L166I+L222V+R242E+ N249E+G251D;
Y11I+I96L+S164G+L166V+L222V+R242E+N249E+ G251D;
Y11I+K19T+D59N+I96L+S164G+L222V+R242E+ N249E;
Y11I+K19T+D59N+I96L+L222V+R242E+N249E+ G251D;
Y11I+K19T+D59N+I96L+S164G+L222I+R242E;
Y11I+K19T+D59N+I96L+S164G+L166V+R242E+ G251D;
Y11I+K19T+D59N+S164G+L166I+L222V+R242E+ G251D;
Y11I+I96L+L222V+R242E+N249E+G251D; Y11I+I96L+ S164G+L222I+R242E;
Y11V+K19T+I96L+L166V+L222V+R242E+G251D;
Y11I+D59N+I96L+S164G+L222I+R242E+G251D;
Y11I+D59N+I96L+S164G+L222V+R242E+N249E+G251D;
Y11I+K19T+D59N+I96L+S164G+L222I+R242E+N249E+G251D;
Y11I+D59N+I96L+S164G+L166V+L222V+R242E+G251D;
Y11V+K19T+D59N+I96L+L222V+R242E+G251D;
Y11I+K19T+5164G+L166I+L222V+R242E+N249E+G251D or
Y11I+D59N+I96L+S164G+L166V+L222V+R242E+N249E+G251D.

An alternative aspect relates to methods for making a food or feed product comprising adding an effective amount of the isolated chymosin polypeptide variant of present invention to the food or feed ingredient(s) and carrying our further manufacturing steps to obtain the food or feed product, such as e.g. a milk-based product and optionally more specifically methods for making cheese such as e.g. Pasta filata, Cheddar, Continental type cheeses, soft Cheese or White Brine Cheese.

Accordingly, present invention relates to a food or feed product comprising a chymosin polypetide variant as described herein.

The polypeptide variant of present invention may also be used to reduce bitterness in cheese and other dairy products as e.g. yoghurt.

In cheese ripening, chymosin cleaves β-casein primarily between Leu192 and Tyr193 (references 2,3). The resulting peptide β(193-209) will be further degraded by proteases to short hydrophobic peptides that taste bitter (reference 4). Since bitterness in dairy applications is most often considered an undesirable feature, it is desirable to develop chymosin variants with lower β-casein cleavage frequency.

Based on intelligent design and a comparative analysis of different variants the present inventors identified a number of amino acid positions that are herein important in the sense that by making a variant in one or more of these positions one may get an improved chymosin variant with a lower β-casein cleavage frequency.

The amino acid numbering as used herein to specify a variant or mutation is done on the mature peptide numbering. For clarification, the mature polypeptide of SEQ ID NO:2 corresponds to SEQ ID NO:4.

As known in the art—different natural wildtype chymosin polypeptide sequences obtained from different mammalian species (such as e.g. bovines, camels, sheep, pigs, or rats) are having a relatively high sequence similarity/identity.

In FIG. 1 this is exemplified by an alignment of herein relevant different chymosin sequences.

In view of this relatively close sequence relationship—it is believed that the 3D structures of different natural wildtype chymosins are also relatively similar.

In the present context—a natural obtained wildtype chymosin (such as bovine chymosin or camel chymosin) may herein be an example of a parent polypeptide—i.e. a parent polypeptide to which an alteration is made to produce a variant chymosin polypeptide of the present invention.

Without being limited to theory—it is believed that the herein discussed chymosin related amino acid positions are of general importance in any herein relevant chymosin enzyme of interest (e.g. chymosins of e.g. bovines, camels, sheep, pigs, rats etc)—in the sense that by making a variant in one or more of these positions one may get an improved chymosin variant in general (e.g. an improved bovine, camel, sheep, pig or rat chymosin variant).

As discussed herein—as a reference sequence for determining the amino acid position of a parent chymosin polypeptide of interest (e.g. camel, sheep, bovine etc) is herein used the public known mature *Camelius dromedarius* chymosin sequence of SEQ ID NO:2 herein. It may herein alternatively be termed camel chymosin. The sequence is also shown in FIG. 1 herein.

In the present context it is believed that a parent chymosin polypeptide (e.g. from sheep or rat) that has at least 65% sequence identity with the mature polypeptide of SEQ ID NO:2 (camel chymosin) may herein be seen as sufficient structural related to e.g. bovine or camel chymosin in order to be improved by making a variant in any of the amino acid positions as described herein.

Embodiments of the present invention are described below.

DEFINITIONS

All definitions of herein relevant terms are in accordance of what would be understood by the skilled person in relation to the herein relevant technical context.

The term "β-cleavage" or "cleavage of β-casein" means any enzymatic cleavage of β-casein. Such as e.g. cleavage between Leu192 and Tyr193, resulting in the formation of β(193-209) peptide. In one aspect β-cleavage is determined by quantifying the β(193-209) peptide obtained by incubating skim milk with the chymosin variant polypeptide or the camel chymosin, wherein quantification is carried out by RP-HPLC coupled to an ESI-Q-TOF mass spectrometer. Full details of a preferred method of determining β-casein cleavage are described in the Examples.

The term "chymosin" relates to an enzyme of the EC 3.4.23.4 class. Chymosin has a high specificity and predominantly clots milk by cleavage of a single 104-Ser-Phe-|-Met-Ala-108 bond in κ-chain of casein. As a side-activity, chymosin also cleaves β-casein primarily between Leu192 and Tyr193 (references 2,3). The resulting peptide β(193-209) will be further degraded by proteases to short hydrophobic peptides that taste bitter (reference 4). An alternative name of chymosin used in the art is rennin.

The term "chymosin activity" relates to chymosin activity of a chymosin enzyme as understood by the skilled person in the present context.

The skilled person knows how to determine herein relevant chymosin activity.

The term "specific clotting activity" describes the milk clotting activity of a chymosin polypeptide and can be determined according to assays well known in the art. A preferred method for determining the specific clotting activity in terms of IMCU/mg of protein is the standard method developed by the International Dairy Federation (IDF method), which comprises steps, wherein milk clotting activity is determined from the time needed for a visible flocculation of a milk substrate and the clotting time of a sample is compared to that of a reference standard having known milk-clotting activity and the same enzyme composition by IDF Standard 110B as the sample. Samples and reference standards are measured under identical chemical and physical conditions. Full details of a the IDF method are described in the Examples.

As known in the art—the herein relevant so-called C/P ratio is determined by dividing the specific clotting activity (C) with the proteolytic activity (P).

As known in the art—a higher C/P ratio implies generally that the loss of protein during e.g. cheese manufacturing due to non-specific protein degradation is reduced, i.e. the yield of cheese is improved.

The term "isolated variant" means a variant that is modified by the act of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The amino acid numbering as used herein to specify chymosin polypeptide variants of the present invention is done on the mature peptide numbering. In the sequence listing provided with the present application:

SEQ ID NO:1 represents the complete polypeptide sequence of bovine preprochmyosin;

SEQ ID NO:2 represents the complete polypeptide sequence of camel preprochmyosin;

SEQ ID NO:3 represents the polypeptide sequence of mature bovine chymosin;

SEQ ID NO:4 represents the polypeptide sequence of mature camel chymosin.

In other words, SEQ ID NOs:3 and 4 correspond to amino acids 59 to 381 of SEQ ID NOs:1 and 2, respectively. All of the specific substitutions identified herein are identified in relation to the position of the mature chymosin sequence, i.e. in relation to the amino acid numbering of SEQ ID NOs:3 or 4. Insofar as the position is identified in relation to the amino acid numbering of SEQ ID NOs:1 or 2 one has to subtract 58 residues to identify the position in SEQ ID NOs:3 or 4 and vice versa.

The term "mature polypeptide" means a peptide in its final form following translation and any post-translational modifications, such as N terminal processing, C terminal truncation, glycosylation, phosphorylation, etc. In the present context may a herein relevant mature chymosin polypeptide be seen as the active chymosin polypeptide sequence—i.e. without the pre-part and/or pro-part sequences. Herein relevant examples of a mature polypeptide are e.g. the mature polypeptide of SEQ ID NO: 1 (bovine chymosin), which is from amino acid position 59 to amino acid position 381 of SEQ ID NO: 1 or the mature polypeptide of SEQ ID NO:2 (camel chymosin), which is from amino acid position 59 to amino acid position 381 of SEQ ID NO:2.

The term "parent", "parent polypeptide" or "parent polypeptide having chymosin activity" means a polypeptide to which an alteration is made to produce the enzyme variants of the present invention. The parent may be a naturally occurring (wild-type) polypeptide or a variant thereof. In a preferred embodiment of present invention, the parent polypeptide has at least 80%, such as at least e.g. 85%, 95%, 97%, 98%, 99% or 100% sequence identity with the polypeptide of SEQ ID NO:4 (camel chymosin).

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

The term "variant" means a peptide having chymosin activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

The term "wild-type" peptide refers to a nucleotide sequence or peptide sequence as it occurs in nature, i.e. nucleotide sequence or peptide sequence which hasn't been subject to targeted mutations by the act of man.

DRAWINGS

FIG. 1: An alignment of herein relevant different chymosin sequences. The shown "Bos_bovis_chymosin B" is bovine chymosin of SEQ ID NO: 1 herein and the shown "*Camelus_dromedarius*" is camel chymosin of SEQ ID NO:2 herein. Using bovine chymosin of SEQ ID NO: 1 as reference sequence as described herein is can e.g. be seen that bovine chymosin has "V" in position 10 and camel chymosin has "A" in the same position 10. It may e.g. also be seen that bovine/Rat have "Q" in position 352 and Camel/*C._bactrianus* have "E" in the same position 352.

In relation to the chymosin sequences shown in FIG. 1—sheep has 94.5% sequence identity with bovine SEQ ID NO: 1; C._bactrianus has 83.2% sequence identity with bovine SEQ ID NO: 1; Camelus_dromedarius (camel chymosin of SEQ ID NO:2) has 84% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of mature polypeptide sequences of e.g. sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

Figure 3:
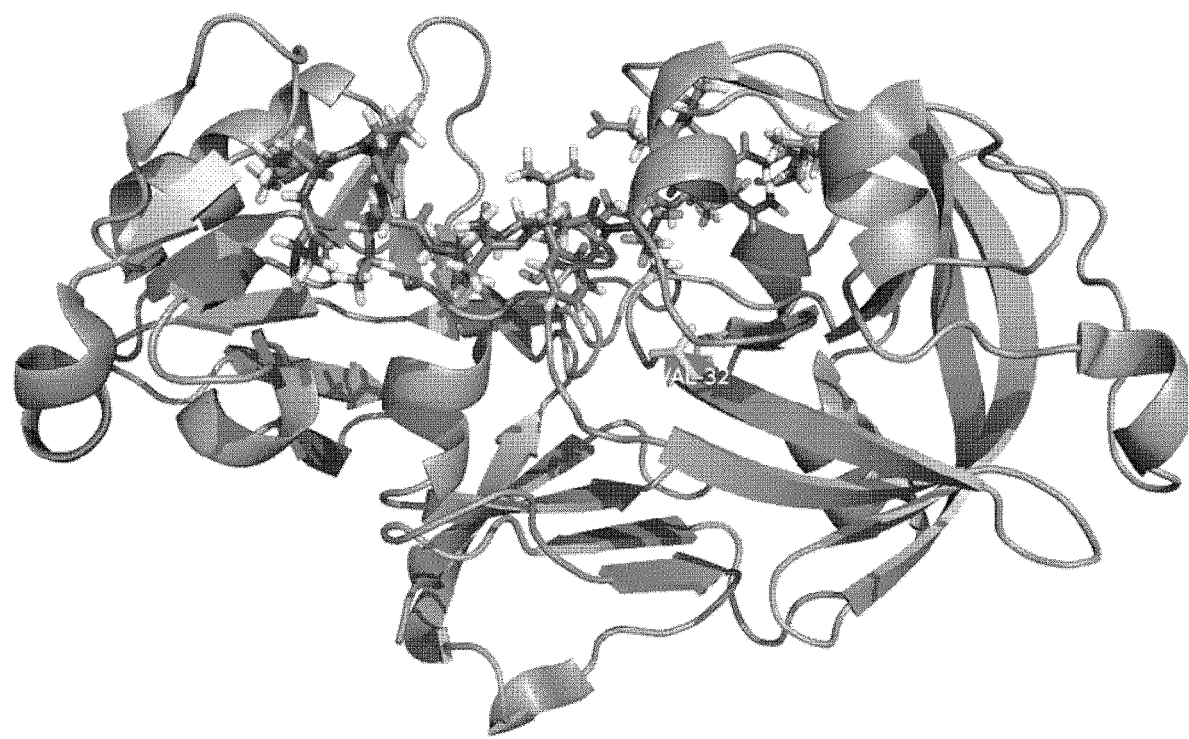

FIGS. 2 and 3:

3D structure of camel chymosin (PDB: 4AA9) with a model of bound β-casein shown in purple. The β-casein is placed in the chymosin substrate binding cleft with the scissile bond between residues 192 and 193. Camel chymosin residues V32, L130, and S132 are highlighted in green.

FIG. 4:

3D structure of camel chymosin (PDB: 4AA9). Camel chymosin residues V32 and L12 are highlighted in green.

DETAILED DESCRIPTION OF THE INVENTION

Determining the Amino Acid Position of a Chymosin of Interest

As discussed above—as a reference sequence for determining the amino acid position of a herein relevant chymosin polypeptide of interest (e.g. camel, sheep, bovine etc.) is herein used the public known camel chymosin sequence disclosed as SEQ ID NO:2 herein.

The amino acid sequence of another chymosin polypeptide is aligned with the polypeptide disclosed in SEQ ID NO: 1, and based on the alignment, the amino acid position number corresponding to any amino acid residue in the polypeptide disclosed in SEQ ID NO: 1 is determined using the ClustalW algorithm as described in working Example 1 herein.

Based on above well-known computer programs—it is routine work for the skilled person to determine the amino acid position of a herein relevant chymosin polypeptide of interest (e.g. camel, sheep, bovine etc.).

In FIG. 1 herein is shown an example of an alignment.

Just as an example—in FIG. 1 can e.g. be seen that herein used bovine reference SEQ ID NO: 1 has a "G" in position 50 and "Camelus_dromedarius" (SEQ ID NO:2 herein) has an "A" in this position 50.

Nomenclature of Variants

In describing the variants of the present invention, the nomenclature described below is adapted for ease of reference. The accepted IUPAC single letter or three letter amino acid abbreviations are employed.

The specific variants discussed in this "nomenclature" section below may not be herein relevant variants of the present invention—i.e. this "nomenclature" section is just to describe the herein relevant used nomenclature as such. As indicated above, the amino acid numbering used to specify chymosin polypetide variants of the present invention is based on the position of the amino acid in the mature chymosin polypeptide sequence.

Substitutions. For an amino acid substitution, the following nomenclature is used: Original amino acid, position, substituted amino acid.

Accordingly, a theoretical substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. A substitution e.g. designated "226A" refers to a substitution of a parent amino acid (e.g. T, Q, S or another parent amino acid) with alanine at position 226. Likewise, a substitution designated "A226" or "A226X" refers to a substitution of an alanine in position 226 with another unspecified amino acid.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different substitutions. Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants:

"Tyr167Gly+Arg170Gly", "Tyr167Gly+Arg170Ala", "Tyr167Ala+Arg170Gly", and "Tyr167Ala+Arg170Ala".

Preferred Variants:

As outlined in the Examples below, the inventors have made a number of preferred chymosin polypeptide variants that cleave β-casein with a lower frequency than the corresponding parent polypeptide while at least maintaining its clotting activity.

Preferred Variants with Reduced β-Casein Cleavage Frequency:

The isolated chymosin polypeptide variants of the present invention have a specific clotting activity (IMCU/mg total protein) that is at least 80% of the specific clotting activity of isolated camel chymosin polypeptide characterized by SEQ ID NO:4, including a specific clotting activity (IMCU/mg total protein) that is at least 85%, at least 90%, at least 95% or at least 97% of the specific clotting activity of isolated camel chymosin polypeptide characterized by SEQ ID NO:4.

The isolated chymosin polypeptide variant of present invention may be derived from a parent polypeptide has at least 80%, such as at least e.g. 80%, 85%, 95%, 97%, 98%, 99% sequence identity with the polypeptide of SEQ ID NO:4 (camel chymosin).

The isolated chymosin polypeptide variant of present invention may comprise one or more amino acid substitutions, deletions or insertions, wherein the one or more substitution, deletion or insertion is specified in relation to the amino acid sequence of SEQ ID NO:4: Y11, L130, S132, V32, S226, R266, L12, V221, S255, S277, L222, L253, M157, V260, S271, H76, K19, V183, S164, I263, V51, T239, Y307, R67, G251, R61, Q288, E83, D59, V309, S273, G251, S154, Y21, V203, L180, E294, G289, L215, D144, I303, L105, T284, Y127, V248, K321, V205, E262, K231, R316, M256, D158, D59, N249, L166, R242 or I96 such as e.g. Y11I, Y11V, L130I, S132A, V32L, S226T, R266V, L12M, V221M, S255Y, S277N, L222I, L253I, M157L, V260T, S271P, H76Q, K19T, V183I, S164G, I263L, V51L, T239S, Y307F, R67Q, G251D, R61Q, Q288E, E83S, D59N, V309I, S273Y, G251W, S154A, Y21S, V203A, L180I, E294Q, G289S, L215V, D144Q, I303L, L105E, T284S, Y127F, V248I, K321P, V205I, E262T, K231N, R316L, M256L, D158S, D59N, N249E, L166V, R242E and/or I96L.

In a related aspect, the isolated chymosin polypeptide variant of present invention may comprise a combination of substitutions, wherein the combination of substitutions is selected from a list comprising:
Y11+K19+D59+I96+S164+L166+L222+R242+N249+G251; Y11+K19+D59+I96+S164+L222+R242+G251; Y11+K19+D59+I96+S164+L166+R242+N249+G251+L253; Y11+K19+I96+S164+L166+R242+N249+G251; Y11+K19+D59+I96+S164+L222+R242+N249+G251; Y11+K19+I96+S164+L166+L222+R242+N249+G251; Y11+K19+D59+I96+S164+L222+R242+N249; Y11+K19+D59+I96+S164+L166+R242+G251; Y11+I96+S164+L222+R242; Y11+D59+I96+S164+L222+R242+G251 or Y11I+K19+D59+I96+S164+ +R242+N249+G251 such as e.g. Y11I+K19T+D59N+I96L+S164G+L166V+L222I+R242E+N249E+G251D; Y11V+K19T+D59N+I96L+S164G+L222V+R242E+G251D; Y11V+K19T+D59N+I96L+S164G+L166I+R242E+N249E+G251D+L253I; Y11I+K19T+I96L+S164G+L166V+R242E+N249E+G251D; Y11V+K19T+D59N+I96L+S164G+L222V+R242E+N249E+G251D; Y11V+K19T+I96L+S164G+L166V+L222V+R242E+N249E+G251D; Y11I+K19T+D59N+I96L+S164G+L222V+R242E+N249E; Y11I+K19T+D59N+I96L+S164G+L166V+R242E+G251D; Y11I+I96L+S164G+L222I+R242E; Y11I+D59N+I96L+S164G+L222I+R242E+G251D or Y11I+K19T+D59N+I96L+S164G+L222I+R242E+N249E+G251D and wherein each substitution is specified in relation to the amino acid sequence of SEQ ID NO:4.

In a related aspect, the variant may comprise alterations in one or more specified positions compared to a parent polypeptide having chymosin activity, wherein in the alteration is comprising a substitution, a deletion or an insertion in at least one amino acid position corresponding to any of positions 11, 130, 132, 32, 226, 266, 12, 221, 255, 277, 222, 253, 157, 260, 271, 76, 19, 183, 164, 263, 51, 239, 307, 67, 251, 61, 288, 83, 59, 309, 273, 251, 154, 21, 203, 180, 294, 289, 215, 144, 303, 105, 284, 127, 248, 321, 205, 262, 231, 316, 256, 158, 59, 249, 166, 242 or 96, wherein the amino acid position of the parent polypeptide is determined by an alignment of the parent polypeptide with the mature polypeptide of SEQ ID NO:2 (camel chymosin) and the parent polypeptide has at least 65% sequence identity with the mature polypeptide of SEQ ID NO:2 (camel chymosin), which is from amino acid position 59 to amino acid position 381 of SEQ ID NO:2, wherein the isolated chymosin polypeptide variant cleaves β-casein with a lower frequency than the corresponding parent polypeptide.

In a preferred embodiment the parent polypeptide has at least 80%, such as at least e.g. 85%, 95%, 97%, 98%, 99% sequence identity with the mature polypeptide of SEQ ID NO:2 (camel chymosin).

Preferably, an isolated chymosin polypeptide variant as described herein is a variant, wherein the variant has a lower β-casein cleavage frequency as compared to the parent peptide from which the variant is derived.

More preferably, an isolated chymosin polypeptide variant as described herein is a variant, wherein the variant has
  a chymosin activity giving lower β-casein cleavage frequency as compared to the bovine chymosin comprising the mature polypeptide of SEQ ID NO: 1 herein; and
  a chymosin activity giving a lower β-casein cleavage frequency as compared to the camel chymosin comprising the mature polypeptide of SEQ ID NO:2 herein.

As discussed above—as a reference sequence for determining the amino acid position of a herein relevant chymosin polypeptide of interest (e.g. camel, sheep, bovine etc.) is herein used the mature peptide of the publicly known camel chymosin sequence disclosed as SEQ ID NO:2 herein.

As discussed above—based on e.g. the computer sequence alignment programs discussed herein—it is routine work for the skilled person to determine the here—in relevant amino acid position of a herein relevant chymosin polypeptide of interest (e.g. camel, sheep, bovine etc.).

The term "the parent polypeptide has at least 65% sequence identity with the mature polypeptide of SEQ ID NO:2 (camel chymosin)" may be seen as relating to a sequence based limitation of the parent chymosin polypeptide used to make a herein relevant variant thereof.

In a preferred embodiment—the parent polypeptide has at least 92% sequence identity with the mature polypeptide of SEQ ID NO:2 (camel chymosin), more preferably the parent polypeptide has at least 95% sequence identity with the mature polypeptide of SEQ ID NO:2 (camel chymosin) and even more preferably the parent polypeptide has at least 97% sequence identity with the mature polypeptide of SEQ ID NO:2 (camel chymosin). It may be preferred that the parent polypeptide is the mature polypeptide of SEQ ID NO:2 (Camel chymosin).

As understood by the skilled person in the present context—a herein relevant parent polypeptide having chymosin activity may already e.g. be a variant of e.g. a corresponding wildtype chymosin.

Said in other words, a herein relevant isolated chymosin polypeptide variant may comprise alterations (e.g. substitutions) in other positions than the positions claimed herein.

In relation to the chymosin sequences shown in FIG. 1 herein—sheep has 94.5% sequence identity with bovine SEQ ID NO: 1; C._bactrianus (camel) has 83.2% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of e.g. mature sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

Preferably, an isolated bovine chymosin polypeptide variant as described herein is a variant, wherein the variant has a chymosin activity giving a lower β-casein cleavage frequency as compared to the β-casein cleavage frequency of camel chymosin comprising the mature polypeptide of SEQ ID NO:2.

As discussed above—in working examples herein were made variants using the polypeptide of SEQ ID NO:2 (camel chymosin) as parent polypeptide—such variant may herein be termed camel chymosin variant.

As understood by the skilled person in the present context—an isolated chymosin variant may comprise alterations (e.g. substitutions) in other amino acid positions than given above.

For instance, a camel chymosin variant with e.g. 5-10 alterations (e.g. substitutions) as compared to wildtype camel chymosin polypeptide of SEQ ID NO:2 will still be a parent polypeptide that has at least 95% sequence identity with the mature polypeptide of SEQ ID NO:2 (camel chymosin).

It may be preferred that the isolated camel chymosin variant comprises less than 30 amino acid alterations (e.g. substitutions) as compared to the mature polypeptide of SEQ ID NO:2 (camel chymosin) or it may be preferred that the isolated camel chymosin variant comprises less than 20 amino acid alterations (e.g. substitutions) as compared to the mature polypeptide of SEQ ID NO:2 (camel chymosin) or it may be preferred that the isolated camel chymosin variant comprises less than 10 amino acid alterations (e.g. substitutions) as compared to the mature polypeptide of SEQ ID NO:2 (camel chymosin) or it may be preferred that the isolated camel chymosin variant comprises less than 5 amino acid alterations (e.g. substitutions) as compared to the mature polypeptide of SEQ ID NO:2 (camel chymosin).

As understood by the skilled person in the present context—the term "the isolated variant polypeptide has less than 100% sequence identity with the mature polypeptide of SEQ ID NO:2 (camel chymosin)" above relates to that the herein described isolated camel chymosin variant shall not have a polypeptide sequence that is 100% identical to the public known wildtype camel chymosin sequence of SEQ ID NO:2.

A preferred embodiment relates to an isolated camel chymosin polypeptide variant, wherein the alteration comprises a substitution, a deletion or an insertion in at least one amino acid position corresponding to any of positions claimed herein.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions claimed herein.

Preferred parent polypeptide having chymosin activity:
Preferably, the parent polypeptide has at least 80%, such as e.g. 85%, 90%, 95%, 97%, 98%, or 99% sequence identity with the mature polypeptide of SEQ ID NO: 1 (bovine chymosin) and/or SEQ ID NO:2 (camel chymosin).

Just as an example—a herein suitable relevant parent polypeptide could e.g. be bovine chymosin A—as known in the art bovine chymosin A may only have one amino acid difference as compared to bovine chymosin B of SEQ ID NO: 1 herein.

In a preferred embodiment—the parent polypeptide has at least 90% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin). It may be preferred that the parent polypeptide is the mature polypeptide of SEQ ID NO: 1 (bovine chymosin).

As understood by the skilled person in the present context—a herein relevant parent polypeptide having chymosin activity may already e.g. be a variant of e.g. a corresponding wildtype chymosin.

For instance, a bovine chymosin variant with e.g. 5-10 alterations (e.g. substitutions) as compared to mature wildtype bovine chymosin polypeptide of SEQ ID NO: 1 will still be a parent polypeptide that has at least 95% sequence identity with the mature polypeptide of SEQ ID NO: 1 (Bovine chymosin).

Said in other words and in general—a herein relevant isolated chymosin polypeptide variant may comprise alterations (e.g. substitutions) in other positions than the positions claimed herein.

As understood by the skilled person in the present context—a parent polypeptide that has at least 90% sequence identity with the mature polypeptide of SEQ ID NO:2 (Camel) is still within the SEQ ID NO: 1 (Bovine) based sequence identity requirement i.e. it will be a parent polypeptide that has at least 65% sequence identity with the mature polypeptide of SEQ ID NO: 1 (bovine chymosin).

In a preferred embodiment—the parent polypeptide has at least 92% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin). It may be preferred that the parent polypeptide is the mature polypeptide of SEQ ID NO: 1 (bovine chymosin).

As understood by the skilled person in the present context—an isolated chymosin variant may comprise alterations (e.g. substitutions) in other amino acid positions than given above.

For instance, a bovine chymosin variant with e.g. 5-10 alterations (e.g. substitutions) as compared to wildtype bovine chymosin polypeptide of SEQ ID NO: 1 will still be a parent polypeptide that has at least 95% sequence identity with the mature polypeptide of SEQ ID NO: 1 (Bovine chymosin).

It may be preferred that the isolated bovine chymosin variant comprises less than 30 amino acid alterations (e.g. substitutions) as compared to the mature polypeptide of SEQ ID NO: 1 (bovine chymosin) or it may be preferred that the isolated bovine chymosin variant comprises less than 20 amino acid alterations (e.g. substitutions) as compared to the mature polypeptide of SEQ ID NO: 1 (bovine chymosin) or it may be preferred that the isolated bovine chymosin variant comprises less than 10 amino acid alterations (e.g. substitutions) as compared to the mature polypeptide of SEQ ID NO: 1 (bovine chymosin) or it may be preferred that the isolated bovine chymosin variant comprises less than 5 amino acid alterations (e.g. substitutions) as compared to the mature polypeptide of SEQ ID NO: 1 (bovine chymosin).

The camel chymosin polypeptide of SEQ ID NO:2 has 84% sequence identity with the bovine polypeptide of SEQ ID NO: 1 (i.e. the complete SEQ ID NO: 1 from position 1 to 381, which includes pre and pro sequence).

A Method for Making an Isolated Chymosin Polypeptide Variant

As discussed above—as known in the art, the skilled person may, based on his common general knowledge, routinely produce and purify chymosin and chymosin variants.

Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest.

An example of a suitable method to produce and isolate a chymosin (variant or parent) may be by well-known e.g. fungal recombinant expression/production based technology as e.g. described in WO02/36752A2 (Chr. Hansen).

It is also routine work for the skilled person to make alteration at one or more positions in a parent polypeptide having chymosin activity, wherein the alteration is comprising a substitution, a deletion or an insertion in at least one amino acid position.

As known to the skilled person this may e.g. be done by so-called site directed mutagenesis and recombinant expression/production based technology.

It is also routine work for the skilled person to determine if a herein relevant parent polypeptide (e.g. camel or bovine wildtype chymosin) and/or a herein relevant variant has chymosin activity or not. As known in the art chymosin specificity may be determined by the so-called C/P ratio, which is determined by dividing the specific clotting activity (C) with the proteolytic activity (P).

As known in the art—a higher C/P ratio implies generally that the loss of protein during e.g. cheese manufacturing due to non-specific protein degradation is reduced, i.e. the yield of cheese is improved.

As also known in the art, β-casein cleavage and β-casein (including β(193-209)) formation may be determined using standard methods available to the person skilled in the art.

A Method for Making a Milk Based Product

As discussed above—an isolated chymosin polypeptide variant as described herein may be used according to the art—e.g. to make a milk based product of interest (such as e.g. a cheese product).

As discussed above—an aspect of the invention relates to a method for making a food or feed product comprising adding an effective amount of the isolated chymosin polypeptide variant as described herein to the food or feed ingredient(s) and carrying our further manufacturing steps to obtain the food or feed product.

Preferably, the food or feed product is a milk based product and wherein the method comprises adding an effective amount of the isolated chymosin polypeptide variant as described herein to milk and carrying our further manufacturing steps to obtain the milk based product.

For example, the chymosin polypeptide variant of the present invention may be added to a milk-based product after fermentation of the milk. In one aspect the chymosin polypeptide variant of the present invention is added for coagulation of a fermented milk product as part of a method of producing cheese.

The milk may e.g. be soy milk, sheep milk, goat milk, buffalo milk, yak milk, lama milk, camel milk or cow milk.

The milk based product may e.g. be a fermented milk product such as a quark or a cheese.

Food and Feed Products

The present invention also provides food and feed products comprising a chymosin polypetide variant of the present invention or a chymosin polypeptide variant obtainable according to a method of the present invention. The food and feed product is preferably a fermented food product, such as a fermented milk product, including cheese and quark.

In yet a related aspect, the present invention relates to a method for making a food or feed product comprising adding an effective amount of the isolated chymosin polypeptide variant according to the invention. Preferably, the food or feed product is a milk-based product.

The chymosin polypetide variant of present invention may also be used in a process for making cheese, such as e.g. to reduce bitterness in cheese.

EXAMPLES

Example 1

Alignment and Numbering of Chymosin Protein Sequences and Variant Sequences

Chymosin protein sequences were aligned using the ClustalW algorithm as provided by the EBI (EBI, tools, multiple sequence alignment, CLUSTALW", http://www.ebi.ac.uk/Tools/msa/clustalw2/) and as described in Larkin M A, Blackshields G, Brown N P, Chenna R, McGettigan P A, McWilliam H, Valentin F, Wallace I M, Wilm A, Lopez R, Thompson J D, Gibson T J, Higgins D G (2007). Bio-informatics 23(21), 2947-2948.

ClustalW2 settings for multiple sequence alignments were Protein weight Matrix=BLOSUM, GAP open=10, GAP EXTENSION=0.05, GAP DISTANCES=8, No End Gaps, ITERATION=none, NUMITER=1, CLUSTERING=NJ As a reference sequence the bovine chymosin B prepro-chymosin was used (Gen-bank accession number P00794—disclosed herein as SEQ ID NO: 1), where the N-terminal Methionin has number 1 (MRCL) and the C-terminal Isoleucin (in the protein sequence ... LAKAI) has number 381.

Example 2

Design of Chymosin Variants

Chymosin variants were designed using different strategies.

When there is referred to camel chymosin there is referred to camel chymosin comprising the mature polypeptide of SEQ ID NO:2 herein.

Camel chymosin of SEQ ID NO:2 may be seen as a herein relevant parent polypeptide having chymosin activity used to make camel chymosin variants thereof. When there is referred to bovine chymosin there is referred to bovine chymosin comprising the polypeptide of SEQ ID NO: 1 herein.

Bovine chymosin of SEQ ID NO: 1 may be seen as a relevant parent polypeptide having chymosin activity used to make bovine chymosin variants thereof.

Variants 1 to 269 and 367 to 461 of camel chymosin were designed based on an alignment of a large set of public known aspartic protease sequences having an identity of 25% or more compared to bovine chymosin B.

Variations were generally introduced in regions with a high level of amino acid variation between species, while conserved regions were not changed. Amino acid substitutions were chosen based on phylogenetic, structural and experimental information to identify changes with high probability to show beneficial effects on β-casein cleavage. Multiple variations were introduced in each variant construct, ensuring that each single mutation was present in multiple variant constructs to minimize the effect of covariation between various substitutions. Machine learning and statistical analysis of experimental data were used to determine the relative contributions of the amino acid substitutions to measured coagulant performance of the chymosin variants (references 14, 15).

Variants 271 to 366 were designed based on detailed structural analysis of bovine chymosin (PDB code: 4AA8) and camel chymosin (PDB code: 4AA9). Variations were chosen based on the chemical nature of the respective amino acid side chains and their expected impact on either casein substrate binding or general enzyme properties. Most of the amino acid substitutions in variants 271 to 346 were made in sequence positions either within or in close structural proximity to the substrate binding cleft, or in secondary structural elements that get into contact with the bound casein substrate. Furthermore, changes were made in positions on the protein surface that alter the charge profile of these regions (reference 5) and are therefore expected to have an impact on enzyme performance. Variants 347 to 366 were made based on the different structural conformation of the N-terminal sequence in bovine and camel chymosin. Amino acid substitutions were made in positions within the substrate binding cleft that interact with the N-terminus in camel chymosin.

Example 3

Preparation of Chymosin Variant Enzyme Material

All chymosin variants were synthesized as synthetic genes and cloned into a fungal expression vector such as e.g. pGAMpR-C (described in WO02/36752A2)

The vectors were transformed into *E. coli* and plasmid DNA was purified using standard molecular biology protocols, known to the person skilled in the art.

The variant plasmids were individually transformed into an *Aspergillus niger* or *Aspergillus nidulans* strain and protein was produced essentially as described in WO02/36752A2 and purified using standard chromatography techniques.

As known in the art—the skilled person may, based on his common general knowledge, produce and purify chymosin and chymosin variants—such as herein described bovine and camel chymosin variants.

Example 4

Determination of Specific Chymosin Activity 4.1 Determination of Milk Clotting Activity Milk clotting activity was determined using the REMCAT method, which is the standard method developed by the International Dairy Federation (IDF method) Milk clotting activity is determined from the time needed for a visible flocculation of a standard milk substrate prepared from a low-heat, low fat milk powder with a calcium chloride solution of 0.5 g per liter (pH 6.5). The clotting time of a rennet sample is compared to that of a reference standard having known milk-clotting activity and having the same enzyme composition by IDF Standard 110B as the sample. Samples and reference standards were measured under identical chemical and physical conditions. Variant samples were adjusted to approximately 3 IMCU/ml using an 84 mM acetic acid buffer pH 5.5. Hereafter, 200 µl enzyme preparation was added to 10 ml preheated milk (32° C.) in a glass test tube placed in a water bath, capable of maintaining a constant temperature of 32° C.±1° C. under constant stirring. Alternatively, 20 µL enzyme preparation was added to 1 mL preheated milk as described above.

The total milk-clotting activity (strength) of a rennet was calculated in International Milk-Clotting Units (IMCU) per ml relative to a standard having the same enzyme composition as the sample according to the formula:

$$\text{Strength in } IMCU/\text{ml} = \frac{Sstandard \times Tstandard \times Dsample}{Dstandard \times Tsample}$$

Sstandard: The milk-clotting activity of the international reference standard for rennet.

Tstandard: Clotting time in seconds obtained for the standard dilution.

Dsample: Dilution factor for the sample

Dstandard: Dilution factor for the standard

Tsample: Clotting time in seconds obtained for the diluted rennet sample from addition of enzyme to time of flocculation For clotting activity determination of library 1, 3, 4 and 6 variants as well as variants by structural design, the µIMCU method was used instead of the REMCAT method. As compared to REMCAT, flocculation time of chymosin variants in the µIMCU assay was determined by OD measurements in 96-well microtiter plates at 800 nm in a UV/VIS plate reader. A standard curve of various dilutions of a reference standard with known clotting strength was recorded on each plate. Samples were prepared by diluting enzyme in 84 mM acetate buffer, 0.1% triton X-100, pH 5.5. Reaction at 32° C. was started by adding 250 uL of a standard milk substrate containing 4% (w/w) low-heat, low fat milk powder and 7.5% (w/w) calcium chloride (pH≈6.5) to 25 uL enzyme sample. Milk clotting activity of chymosin variants in International Milk-Clotting Units (IMCU) per ml was determined based on sample flocculation time relative to the standard curve.

4.2 Determination of Total Protein Content

Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 5

Determination of β-Casein Cleavage

Determination of β-Casein Hydrolysis Activity

Chymosin mediated proteolysis of milk proteins was characterized by determining profiles of water soluble peptides extracted at pH 4.6. A culture free cheese model made in 96 well plates was used for the study. In brief, 750 μl skim milk from Øllingegård, Denmark added glucono-delta-lactone (GDL) and calcium chloride was aliquoted into the wells of a 96 deep well plate. After 10 min from addition of GDL to the milk, variants of chymosin were added to individual wells of the plate to a final activity of 0.05 IMCU/ml. The formed coagulum was cut after 30 min from addition of rennet by thoroughly stirring the coagulum with a pipette tip; a new tip was used for each well. Subsequently, the plate was left for another 60 min before curd and whey was separated by centrifugation of the plate for 10 min at 2500 g. The milk was kept at 30° C. during renneting, cutting and syneresis. Finally, whey was decanted from the plate and the pellet of rennet curd left in the plate was stored for 4 days at room temperature. Peptides were extracted by adding 500 μl of 0.5 M tri-sodium citrate to each well and gentle shaking the plate for 24 hours at 37° C. The now fully dissolved rennet curd was then precipitated by adding hydrochloric acid to a final pH of 4.4-4.5. The plate was spun down in a centrifuge and the supernatant recovered for further analysis of pH 4.5 soluble peptides.

Profiles of pH 4.5 soluble peptides were determined using RP-HPLC coupled to an ESI-Q-TOF mass spectrometer. The analysis was performed by using a liquid chromatography system (Agilent 1290 infinity, Agilent Technologies A/S, Santa Clara, Calif., USA) coupled to a mass spectrometer (G6540A Q-TOF, Agilent Technologies A/S, Santa Clara, Calif., USA). The column in the LC system was Ascentis Express Peptide ES-C18m, 2.7 μm, 100×2.1 mm (Supelco, Sigma-Aldrich, St. Louis, USA). The mobile phase consisted of eluent A (0.1% formic acid in water) and eluent B (Acetonitrile: 0.1% formic acid in water, 9:1). After equilibration of the column with 2% B, a sample volume of 10 μL was injected. The peptides were separated by gradient elution generated by increasing eluent B from 2% to 50% over 15 column volumes. The flow rate was 0.44 mL/min. Peptides were detected by continuously measuring the UV absorbance at 214 nm. By running MS scans from 100 to 2000 m/z the mass spectra were collected. MS/MS analysis was performed on the two most intense ions from each scan. A MIX sample consisting of equal volume of all samples analyzed was prepared and this sample was analyzed for each 12 samples. MS data were converted from the Agilent .d format to .mzml files using MSConvert ver. 3.0.6618. All further data analysis was done using R 3.1.3. Peptides were identified from MS/MS spectra using R package 'MSGFplus' version 1.05. Search database for peptide identification were limited to the bovine milk proteins: αs1-casein, αs2-casein, β-casein, κ-casein, β-lactoglobulin, α-lactalbumin, lactoperoixdase and lactoferrin. Serine phosphorylation and methionine oxidation were included as variable modifications. R package 'xcms' v. 1.42.0 was used for detecting and grouping peaks across samples in a sample set according to Smith et al. (2006). Massifquant method was used for peak detection and grouping of peaks was based on the density method. Identity was assigned to grouped peaks resulting in quantitative tables of identified peptides including β-casein 193-209.

Statistical Analysis of the Positional and Mutational Effects on β-Casein Cleavage A statistical machine-learning approach and PCA-based analysis was used to determine the effects of all single mutations present in the variants of multi-substitution libraries 1-3, 4 and 6 on cleavage of β-casein at position 192/193.

Results

Multi-Substitution Library 1

Variants of camel chymosin, each having multiple substitutions compared to wild type, were generated and analyzed as described above. All variants have an amino acid sequence identical to camel chymosin (mature polypeptide of SEQ ID NO:2), except for the variations mentioned in the table. Both bovine and camel chymosin were included as references.

Clotting activities were determined using the μIMCU method.

TABLE 1

Cleavage of β-casein at position 192/193 of camel chymosin variants 1-95. Numbers are given in % cleavage of wild type camel chymosin (CHY-MAX M).

| variant | mutations | | | | | β(193-209) |
|---|---|---|---|---|---|---|
| CHY-MAX | | | | | | 795 |
| CHY-MAX M | | | | | | 100 |
| 1 | I96L | G163E | V221M | | | 80 |
| 2 | Y127F | R145Q | Q188E | | | 172 |
| 3 | Y21S | L166V | L253I | | | 110 |
| 4 | N50K | T186S | Y307F | | | 109 |
| 5 | G70N | S277N | R316L | | | 192 |
| 6 | I200V | Y268F | S271P | R316L | | 140 |
| 7 | M157L | T186S | I200V | S273Y | | 276 |
| 8 | D98V | G251D | M256L | V259I | | 136 |
| 9 | R67Q | H76Q | S132A | V248I | S271P | 41 |
| 10 | Y21S | D98V | V221K | T239S | R316L | 216 |
| 11 | V136I | T186S | V221K | I263L | S277N | 246 |
| 12 | N50K | L222I | S255Y | | | 136 |
| 14 | R67Q | V221M | M256L | | | 126 |
| 15 | G70D | L166V | V317L | | | 1127 |
| 16 | R67Q | L130I | M157L | | | 48 |
| 17 | Y21S | R61S | H146R | | | 174 |
| 18 | V136I | V221M | L222I | S226T | | 67 |

TABLE 1-continued

Cleavage of β-casein at position 192/193 of camel chymosin variants 1-95. Numbers are given in % cleavage of wild type camel chymosin (CHY-MAX M).

| variant | mutations | | | | | β(193-209) |
|---|---|---|---|---|---|---|
| 19 | S132A | R254S | V259I | Y307F | | 54 |
| 20 | Y21S | H76Q | Y307F | V317L | | 123 |
| 21 | D158S | L166V | V248I | F223V | G251D | 307 |
| 22 | G70D | S74F | D158S | R254S | S277N | 195 |
| 23 | N50K | D59N | M157L | M256L | G289S | 124 |
| 24 | M142I | V221K | T284S | | | 266 |
| 25 | R61S | R67Q | K231N | | | 135 |
| 26 | V32L | I96L | S277N | | | 25 |
| 27 | V183I | G251W | M256L | | | 134 |
| 28 | M157L | T239S | D279E | | | 164 |
| 29 | V248I | S226T | E294Q | | | 128 |
| 30 | S74F | L166V | T186S | V203A | | 101 |
| 32 | R67Q | Y127F | V221K | G251W | | 232 |
| 33 | L130I | M142I | I200V | V259I | E294Q | 87 |
| 34 | G70D | I96L | I200V | D267M | D279E | 161 |
| 35 | G70N | K231N | S273Y | T284S | G289S | 174 |
| 36 | V32L | G70N | M142I | | | 1024 |
| 37 | V203A | S273Y | L295K | | | 115 |
| 38 | S74F | G244D | S271P | | | 122 |
| 39 | L130I | G163E | Y307F | | | 51 |
| 40 | R61S | L166V | T239S | | | 85 |
| 41 | R254S | D279E | L295K | | | 999 |
| 42 | L130I | T239S | S277N | L295K | | 68 |
| 43 | G70D | V183I | Q188E | G289S | | 198 |
| 44 | R61S | G163E | M256L | S277N | | 192 |
| 46 | D98V | H146R | V203A | I263L | S271P | 85 |
| 47 | S132A | V221M | S255Y | S273Y | V317L | 19 |
| 48 | H76Q | L222I | G251W | | | 60 |
| 49 | V221K | V248I | S255Y | | | 158 |
| 50 | H76Q | K231N | G244D | | | 68 |
| 51 | Y127F | S132A | D158S | | | 35 |
| 52 | D59N | S271P | T284S | | | 119 |
| 53 | G70D | T186S | L253I | | | 110 |
| 54 | R61Q | V221K | K231N | D267M | | 198 |
| 55 | V221M | V248I | L253I | L295K | | 73 |
| 56 | V183I | V248I | G244D | T284S | | 102 |
| 57 | D59N | Y127F | L166V | V183I | S255Y | 130 |
| 58 | N50K | R61S | Y127F | G244D | G251D | 720 |
| 59 | I96L | F223V | G244D | R254S | M256L | 903 |
| 60 | V32L | R61Q | H146R | | | 22 |
| 61 | H146R | D158S | S273Y | | | 949 |
| 62 | R61Q | M142I | G289S | | | 182 |
| 63 | S74F | V259I | Y268F | | | 971 |
| 64 | G70N | D98V | V136I | | | 861 |
| 65 | D59N | V203A | R254S | | | 112 |
| 66 | T239S | I263L | D267M | T284S | | 124 |
| 67 | I96L | M142I | R145Q | H146R | | 780 |
| 68 | V32L | E294Q | R316L | V317L | | 27 |
| 69 | V32L | G163E | T186S | Q188E | L295K | 752 |
| 70 | R61Q | V136I | Y268F | T284S | Y307F | 795 |
| 71 | S132A | Q188E | F223V | | | 627 |
| 72 | H76Q | I96L | D158S | | | 89 |
| 73 | V136I | R145Q | G251D | | | 127 |
| 74 | R61Q | D98V | V317L | | | 174 |
| 75 | Y21S | D59N | I263L | | | 135 |
| 76 | I200V | G251D | G289S | | | 725 |
| 77 | D98V | M157L | V183I | | | 84 |
| 78 | S226T | G244D | I263L | G289S | | 51 |
| 79 | Q188E | G251D | S271P | D279E | | 160 |
| 80 | N50K | D158S | V203A | E294Q | | 682 |
| 81 | V203A | V248I | G251W | L253I | Y268F | 152 |
| 82 | R61S | V183I | L222I | L253I | D267M | 100 |
| 84 | G70D | L130I | Y268F | | | 49 |
| 85 | Y127F | D267M | E294Q | | | 163 |
| 88 | F223V | V248I | I263L | | | 248 |
| 89 | G70N | R254S | S255Y | Y268F | | 105 |
| 90 | D59N | V248I | L222I | V248I | | 90 |
| 91 | F223V | G251W | S273Y | D279E | | 352 |
| 92 | R67Q | G70N | H146R | Q188E | S226T | 84 |
| 93 | S74F | H76Q | M142I | M157L | G163E | 99 |
| 94 | R61Q | S226T | T239S | V248I | G251W | 53 |
| 95 | V32L | L130I | R145Q | L222I | D279E | 5 |

In Table 1 are shown camel chymosin variants with data on cleavage of β-casein at position 192/193. Since all enzyme variants were used at a normalized concentration of 0.05 IMCU/mL in the experiments, low β-casein cleavage indicates high specificity of the respective variant for κ-casein 104/105 over β-casein 192/193 cleavage, rather than low general enzymatic activity.

Variants with half or less than wild type proteolytic activity on β-casein are highlighted in bold (variants 9, 16, 26, 39, 47, 51, 60, 68, 78, 84, 95). In those, mutations V32L, L130I, and S132A are overrepresented, compared to the mutational pattern present in the entire variant set shown. Four out of six variants with mutation V32L, four out of six variants with mutation L130I, and three out of five variants with mutation S132A show β-casein 192/193 cleavage equal or less than 50% of wild type camel chymosin.

In the three-dimensional structure of camel chymosin, position V32 is interacting with the P1 residue of the substrate peptide sequence (FIG. 2), while positions L130 and S132 are interacting with P5" (L130) as well as P2' and P6' (S132), respectively (FIG. 3; references 5-10). The location of the three positions in the chymosin substrate binding site suggests that mutations V32L, L130I, and S132A cause lower β-casein 192/193 cleavage and, thus, lower generation of the β-casein fragment β(193-209) at constant coagulant strengths by direct interaction with κ- and β-casein. Variant 95, which is showing the lowest β-casein 192/193 cleavage throughout the variant set, contains both mutations V32L and L130I. This suggests additivity of the mutational effects on casein substrate specificity.

Multi-Substitution Library 2

Another set of camel chymosin variants, each having multiple substitutions compared to wild type, were generated and analyzed as described. All variants have an amino acid sequence identical to camel chymosin, except for the variations mentioned in the table. Both bovine and camel chymosin were included as references. Clotting activities were determined using the REMCAT method.

TABLE 2

Cleavage of β-casein at position 192/193 of camel chymosin variants 96-143. Numbers are given in % cleavage of wild type camel chymosin (CHY-MAX M).

| variant | mutations | | | | | β(193-209) |
|---|---|---|---|---|---|---|
| CHY-MAX | | | | | | 488 |
| CHY-MAX M | | | | | | 100 |
| 96 | D59N | L222I | G251D | E83S | Q162S | 70 |
| 97 | D59N | L222I | G251W | F17Y | Y21S | 85 |
| 98 | D59N | L222I | G251D | H76Q | S164G | 29 |
| 99 | D59N | L222I | G251D | K62Q | M165E | 94 |
| 100 | D59N | L222I | G251D | Q162S | V155F | 74 |
| 101 | D59N | L222I | G251D | H76Q | V155F | 284 |
| 102 | D59N | L222I | G251D | S273Y | L166V | 75 |
| 103 | D59N | L222I | G251D | Y268F | V198I | 72 |
| 104 | D59N | L222I | G251D | S273Y | F66Y | 64 |
| 105 | D59N | L222I | G251D | M165E | L166V | 70 |
| 106 | D59N | L222I | G251D | H76Q | M165E | 63 |
| 107 | D59N | L222I | G251D | F17Y | S273Y | 76 |
| 108 | D59N | L222I | G251D | L166V | I45V | 84 |
| 109 | D59N | L222I | G251W | L180I | T284S | 84 |
| 110 | D59N | L222I | G251D | V32L | L12M | T284S | 20 |
| 111 | D59N | L222I | G251D | Y21S | L166V | | 61 |
| 112 | D59N | L222I | G251D | V155F | E262T | V32L | 16 |
| 113 | D59N | L222I | G251D | L105E | S164G | | 52 |
| 114 | D59N | L222I | G251W | S154A | V203A | | 105 |
| 115 | D59N | L222I | G251D | Q162S | L166V | | 233 |
| 116 | D59N | L222I | G251W | K19T | R266I | | 100 |
| 117 | D59N | L222I | G251W | I303L | I45V | | 103 |
| 119 | D59N | L222I | G251D | Y21S | L215V | L105E | 74 |
| 120 | D59N | L222I | G251D | I96L | T177S | K321P | 86 |
| 121 | D59N | L222I | G251D | F17Y | T284S | V203A | 84 |
| 122 | D59N | L222I | G251D | V32L | K321P | V260T | 13 |
| 123 | D59N | L222I | G251D | V198I | V32L | E83S | 82 |
| 124 | D59N | L222I | G251D | I96L | V203A | V309I | 54 |
| 125 | D59N | L222I | G251D | Y268F | L215V | V32L | 11 |
| 126 | D59N | L222I | G251D | H76Q | L105E | V260T | 41 |
| 127 | D59N | L222I | G251D | Y21S | H76Q | Y268F | 30 |
| 128 | D59N | L222I | G251D | Y21S | I45V | F223A | 295 |
| 129 | D59N | L222I | G251D | V198I | V203A | K321P | 109 |
| 131 | D59N | L222I | G251D | S164G | R266V | I96L | 39 |
| 132 | D59N | L222I | G251D | H181N | F66Y | V32L | 10 |
| 133 | D59N | L222I | G251D | H181N | R266I | D267Q | 91 |
| 134 | D59N | L222I | G251W | K62Q | V309I | | 103 |
| 135 | D59N | L222I | G251D | Y268F | L12M | D267Q | 64 |
| 136 | D59N | L222I | G251D | L166V | E262T | T177S | 97 |
| 137 | D59N | L222I | G251D | S273Y | T284S | D267Q | 107 |
| 138 | D59N | L222I | G251D | F66Y | Q288E | I96L | 51 |
| 139 | D59N | L222I | G251D | V203A | R266V | F223A | 48 |
| 140 | D59N | L222I | G251D | I303L | S154A | V260T | 59 |
| 141 | D59N | L222I | G251D | Y21S | T284S | I96L | 48 |
| 142 | D59N | L222I | G251D | Q288E | K19T | T177S | 45 |
| 143 | D59N | L222I | G251D | K62Q | Y268F | K19T | 55 |

In Tab. 2 are shown camel chymosin variants with data on cleavage of β-casein at position 192/193. Since all enzyme variants were used at a normalized concentration of 0.05 IMCU/mL in the experiments, low β-casein cleavage indicates high specificity of the respective variant for κ-casein 104/105 over β-casein 192/193 cleavage, rather than low general enzymatic activity.

Variants with less than 25% wild type proteolytic activity on β-casein are highlighted in bold (variants 110, 112, 122, 125, 132). In those, mutation V32L is overrepresented, compared to the mutational pattern present in the entire variant set shown. Five out of six variants with mutation V32L show β-casein 192/193 cleavage equal or less than 25% of wild type camel chymosin. These results support the findings and conclusions of the previous variant set.

Multi-Substitution Library 3

A third set of camel chymosin variants, each having multiple substitutions compared to wild type, were generated and analyzed as described. All variants have an amino acid sequence identical to camel chymosin, except for the variations mentioned in the table. Both bovine and camel chymosin were included as references. Clotting activities were determined using the μIMCU method.

three variants with mutation V32L show β-casein 192/193 cleavage less than 10% of wild type camel chymosin.

Only one variant from this variant set (variant 176) is showing higher than 50% β-casein 192/193 cleavage compared to wild type camel chymosin. This is also the only variant from this set lacking mutation L12M.

Figure 4:
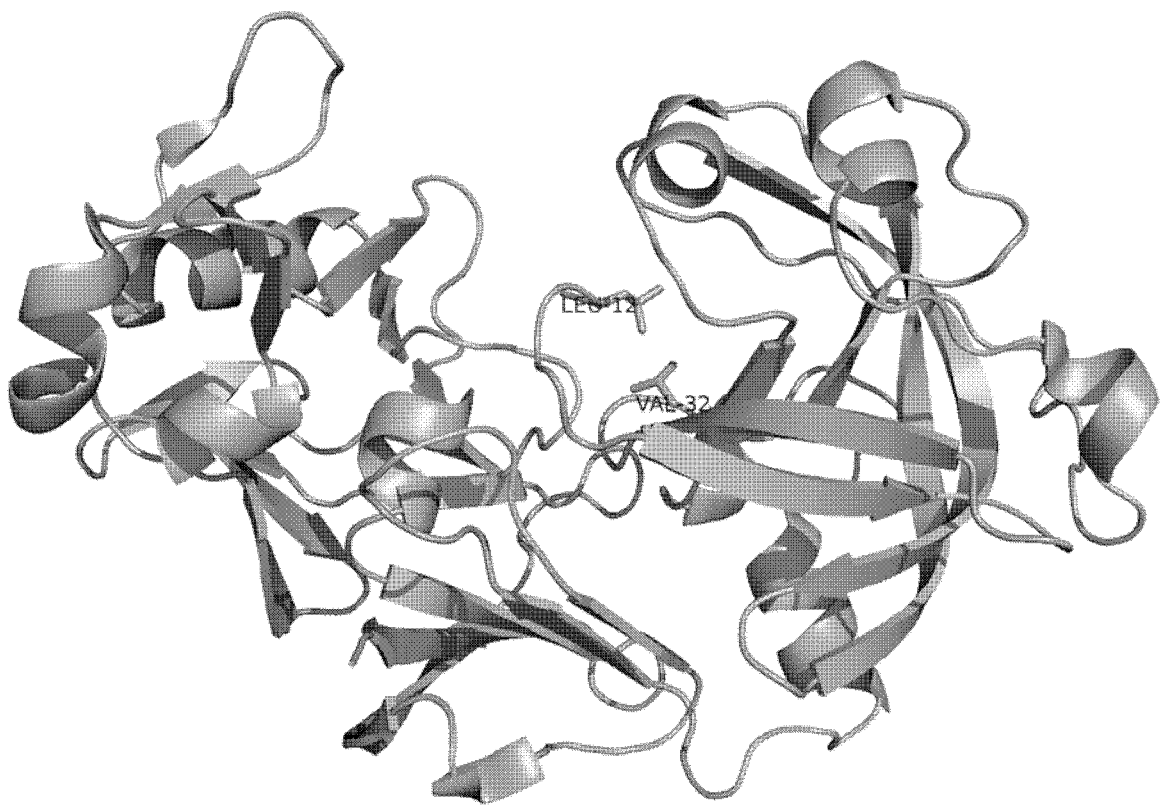

Position L12 is located in the sequence stretch close to the N-terminus of camel chymosin that is bound in the substrate binding cleft of the enzyme (FIG. 4). It has been described that in camel chymosin the N-terminal sequence is blocking the substrate binding cleft of the enzyme when no substrate is bound (reference 5). Casein substrate molecules need to replace this N-terminal sequence in order to bind to the active site and subsequently get cleaved. Mutations in chymosin that are stabilizing this inactive form of the enzyme can consequently reduce substrate binding and, thus, affect casein cleavage specificity. We conclude this mode of action for mutation L12M. In the three-dimensional structure of camel chymosin, positions L12 and V32 are in direct contact with each other. In addition to its direct impact on β-casein

TABLE 3

Cleavage of β-casein at position 192/193 of camel chymosin variants 144-179.
Numbers are given in % cleavage of β-casein of wild type camel chymosin (CHY-MAX M).

| Var. | | | | mutations | | | | | | β (193-209) |
|---|---|---|---|---|---|---|---|---|---|---|
| | | | | CHY-MAX | | | | | | 791 |
| | | | | CHY-MAX M | | | | | | 100 |
| 144 | L12M | Y21S | D59N | H76Q | M165E | V198I | L222I | G251D | Q288E | 20 |
| 146 | L12M | Y21S | D59N | H76Q | M165E | L222I | G251W | S273Y | | 25 |
| 147 | L12M | D59N | H76Q | M165E | V198I | L222I | G251D | S273Y | K321P | 27 |
| 148 | L12M | D59N | H76Q | S154A | M165E | V203A | L222I | G251D | V309I | 23 |
| 149 | L12M | D59N | H76Q | D98V | L222I | | | | | 31 |
| 150 | L12M | K19T | V32L | D59N | H76Q | D144Q | M165E | L222I | G251D | 6 |
| 151 | L12M | Y21S | D59N | H76Q | M165E | V203A | L222I | G251D | E262T | 26 |
| 152 | L12M | V51L | H76Q | M165E | G251D | | | | | 41 |
| 153 | L12M | D59N | F66Y | H76Q | M165E | L180I | L222I | G251D | V309I | 29 |
| 154 | L12M | D59N | H76Q | S154A | M165E | L222I | G251W | Q288E | | 25 |
| 155 | L12M | D59N | H76Q | D98V | M165E | L222I | G251D | E262T | Q288E | 23 |
| 156 | L12M | V51L | D59N | H76Q | L166V | L222I | G251D | | | 17 |
| 157 | L12M | D59N | H76Q | D144Q | M165E | V203A | L222I | | | 30 |
| 158 | L12M | D59N | D144Q | M165E | L166V | L222I | G251D | | | 38 |
| 159 | L12M | K19T | D59N | H76Q | S154A | M165E | V198I | L222I | G251D | 16 |
| 160 | L12M | H76Q | D98V | M165E | L222I | G251W | | | | 36 |
| 161 | L12M | V32L | D59N | H76Q | M165E | L180I | V198I | L222I | G251D | 8 |
| 162 | L12M | D59N | H76Q | S154A | M165E | S273Y | | | | 46 |
| 164 | L12M | V51L | D59N | F66Y | H76Q | M165E | V203A | L222I | G251W | 36 |
| 165 | L12M | V32L | H76Q | M165E | L222I | E262T | | | | 8 |
| 166 | L12M | N50D | D59N | H76Q | M165E | G251W | E262T | | | 40 |
| 168 | V51L | D59N | H76Q | M165E | L180I | L222I | G251D | E262T | | 36 |
| 169 | L12M | D59N | H76Q | M165E | G251D | Q288E | V309I | K321P | | 39 |
| 172 | L12M | N50D | D59N | V203A | L222I | G251D | | | | 40 |
| 173 | L12M | D59N | H76Q | L180I | L222I | G251W | K321P | | | 25 |
| 174 | L12M | Y21S | D59N | M165E | L222I | K321P | | | | 48 |
| 176 | D59N | H76Q | M165E | L166V | V198I | L222I | | | | 63 |
| 178 | L12M | K19T | N50D | D59N | H76Q | M165E | L222I | Q288E | | 30 |
| 179 | L12M | Y21S | N50D | D59N | F66Y | H76Q | D144Q | M165E | L222I | G251D | 36 |

In Tab. 3 are shown camel chymosin variants with data on cleavage of β-casein at position 192/193. Since all enzyme variants were used at a normalized concentration of 0.05 IMCU/mL in the experiments, low β-casein cleavage indicates high specificity of the respective variant for κ-casein 104/105 over β-casein 192/193 cleavage, rather than low general enzymatic activity.

Variants with less than 10% wild type proteolytic activity on β-casein are highlighted in bold (variants 150, 161, 165). In those, mutation V32L is overrepresented, compared to the mutational pattern present in the entire variant set shown. All binding, V32L might as well stabilize the inactive form of the enzyme. Since variants containing both mutations (150, 161, 165) show lowest β-casein 192/193 cleavage amongst all variants of this set, their impact on casein substrate specificity seems to be additive.

Mutational Analysis of Multi-Substitution Libraries 1-3

A statistical analysis of the positional and mutational effects on β-casein cleavage was performed based on the proteolytic data of libraries 1-3. The most beneficial mutations for decreased β-casein cleavage are shown in table 4.

TABLE 4

Mutational contributions (mean) to reduced β-casein 192/193 cleavage and standard deviations (sd) based on statistical analysis.

| mutation | mean | sd |
|---|---|---|
| L130I | 2.43E−01 | 4.32E−02 |
| S132A | 1.96E−01 | 6.49E−02 |
| V32L | 1.87E−01 | 5.95E−02 |
| S226T | 1.67E−01 | 4.04E−02 |
| R266V | 1.54E−01 | 4.35E−02 |
| L12M | 1.45E−01 | 2.23E−02 |
| V221M | 1.35E−01 | 3.48E−02 |
| S255Y | 1.09E−01 | 4.62E−02 |
| S277N | 1.05E−01 | 4.15E−02 |
| L222I | 9.64E−02 | 2.22E−02 |
| L253I | 8.78E−02 | 3.13E−02 |
| M157L | 8.67E−02 | 3.50E−02 |
| V260T | 8.33E−02 | 3.76E−02 |
| S271P | 8.04E−02 | 3.21E−02 |
| H76Q | 7.68E−02 | 2.67E−02 |
| K19T | 6.76E−02 | 2.57E−02 |
| V183I | 6.64E−02 | 3.05E−02 |
| S164G | 6.51E−02 | 2.15E−02 |
| I263L | 6.37E−02 | 2.77E−02 |
| V51L | 6.25E−02 | 3.01E−02 |
| T239S | 6.25E−02 | 3.32E−02 |
| E262T | 6.03E−02 | 2.61E−02 |
| K231N | 5.78E−02 | 2.93E−02 |
| R316L | 5.22E−02 | 4.55E−02 |
| I96L | 4.81E−02 | 3.22E−02 |

Based on the obtained results it is concluded that mutations shown in table 4 reduce β-casein 192/193 cleavage, with the above described mutations L130I, S132A, V32L, and L12M being amongst the mutations with the strongest impact (highlighted in bold in table 4).

Since the mutations shown in table 4 cause less generation of the C-terminal fragment of β-casein, β(193-209), they represent preferred mutations in chymosin variants for making cheese with less bitter taste due to reduced cleavage of β-casein.

Multi-Substitution Library 4

Another set of camel chymosin variants, each having multiple substitutions compared to wild type, were generated and analyzed as described above. All variants have an amino acid sequence identical to camel chymosin (mature polypeptide of SEQ ID NO:2), except for the variations mentioned in the table. Camel chymosin (CHY-MAX M) is included as reference.

Clotting activities were determined using the μIMCU method.

TABLE 5

Cleavage of β-casein at position 192/193 of camel chymosin variants 180-222. Numbers are given in % cleavage of β-casein of wild type camel chymosin(CHY-MAX).

| variant | mutations | | | | | | | | β(193-209) |
|---|---|---|---|---|---|---|---|---|---|
| CHY-MAX M | | | | | | | | | 100 |
| 180 | H76Q | S132A | S164G | L222I | N249D | G251D | | | 14 |
| 181 | Y21S | D59N | H76Q | S164G | L166V | N249D | G251D | S273Y | 53 |
| 182 | D59N | H76Q | S164G | L222I | R242E | S273Y | V309I | | 35 |
| 183 | D59N | H76Q | L130I | L166V | L222I | N249D | G251D | S273Y | 22 |
| 184 | Y21S | D59N | S164G | L222I | R242E | G251D | S273Y | V309I | 42 |
| 185 | K19T | Y21S | D59N | H76Q | S132A | S164G | L222I | G251D | S273Y | 12 |
| 186 | D59N | H76Q | I96L | L130I | S164G | L222I | R242E | G251D | 9 |
| 187 | H76Q | S164G | L166V | L222I | S226T | S273Y | | | 26 |
| 188 | K19T | D59N | I96L | S164G | L222I | G251D | | | 33 |
| 189 | Y21S | H76Q | S164G | L222I | R242E | G251D | S273Y | | 23 |
| 190 | H76Q | I96L | S164G | L222I | R242E | G251D | S273Y | | 23 |
| 191 | H76Q | S164G | L222I | N249D | G251D | S273Y | V309I | | 31 |
| 192 | K19T | D59N | H76Q | S164G | L222I | N249D | S273Y | | 20 |
| 193 | Y21S | D59N | H76Q | S164G | L222I | S226T | G251D | S273Y | V309I | 21 |
| 194 | H76Q | S164G | L166V | L222I | R242E | G251D | S273Y | | 21 |
| 195 | D59N | H76Q | I96L | S164G | L222I | S226T | N249D | G251D | S273Y | 19 |
| 196 | D59N | H76Q | L130I | S164G | L166V | L222I | G251D | S273Y | V309I | 14 |
| 197 | D59N | S132A | S164G | L222I | R242E | N249D | G251D | S273Y | 12 |
| 198 | H76Q | I96L | S164G | G251D | S273Y | V309I | | | 39 |
| 199 | D59N | H76Q | L130I | S164G | G251D | V309I | | | 13 |
| 200 | K19T | D59N | S164G | L166V | L222I | S226T | G251D | S273Y | 28 |
| 201 | D59N | H76Q | I96L | S132A | S164G | L222I | S226T | G251D | S273Y | 8 |
| 202 | K19T | D59N | I96L | S164G | L166V | L222I | G251D | S273Y | 17 |
| 203 | K19T | D59N | H76Q | L130I | S164G | L222I | S226T | G251D | S273Y | 11 |
| 204 | K19T | D59N | H76Q | S132A | L222I | G251D | S273Y | V309I | 18 |
| 205 | H76Q | L130I | L222I | S226T | G251D | S273Y | | | 14 |
| 206 | K19T | Y21S | D59N | H76Q | L130I | S164G | L222I | S273Y | 15 |
| 207 | Y21S | D59N | H76Q | I96L | S164G | L222I | N249D | G251D | S273Y | 28 |
| 208 | K19T | D59N | H76Q | S164G | R242E | N249D | G251D | S273Y | 24 |
| 209 | D59N | H76Q | S164G | L222I | S226T | R242E | | | 15 |
| 210 | D59N | H76Q | I96L | S132A | S164G | L166V | L222I | G251D | S273Y | 11 |
| 211 | D59N | H76Q | S132A | S164G | L166V | S273Y | | | 17 |
| 212 | Y21S | D59N | S164G | L222I | S226T | N249D | G251D | S273Y | 33 |
| 213 | D59N | H76Q | L130I | S132A | S164G | L222I | R242E | G251D | S273Y | 7 |
| 214 | D59N | S164G | L166V | L222I | N249D | G251D | S273Y | V309I | 32 |
| 215 | D59N | H76Q | I96L | S164G | L222I | S226T | G251D | S273Y | V309I | 18 |
| 216 | K19T | D59N | H76Q | L166V | L222I | R242E | G251D | S273Y | 43 |
| 217 | Y21S | D59N | H76Q | I96L | L222I | S273Y | | | 56 |

TABLE 5-continued

Cleavage of β-casein at position 192/193 of camel chymosin variants 180-222.
Numbers are given in % cleavage of β-casein of wild type camel chymosin(CHY-MAX).

| variant | mutations | | | | | | | | β(193-209) |
|---|---|---|---|---|---|---|---|---|---|
| 218 | D59N | H76Q | I96L | L130I | S164G | L222I | N249D | G251D | S273Y | 14 |
| 219 | L130I | S164G | L222I | S273Y | | | | | | 19 |
| 220 | K19T | Y21S | H76Q | S164G | L222I | G251D | S273Y | | | 36 |
| 221 | Y21S | D59N | H76Q | L130I | S132A | S164G | L222I | G251D | S273Y | 11 |
| 222 | D59N | H76Q | S226T | R242E | G251D | S273Y | | | | 54 |

In table 5 are shown camel chymosin variants with data on cleavage of β-casein 192/193. All variants reveal between 44% and 93% reduced proteolytic activity compared to wild type camel chymosin.

Mutational Analysis of Multi-Substitution Library 4

A statistical analysis of the positional and mutational effects on β-casein cleavage was performed based on the proteolytic data of library 4 variants. The most beneficial mutations for decreased β-casein cleavage are shown in table 6.

TABLE 6

Mutational contributions (mean) to reduced β-casein 192/193 cleavage and standard deviations (sd) based on statistical analysis.

| mutation | mean | sd |
|---|---|---|
| S132A | 1.10E+00 | 1.17E−01 |
| L130I | 1.07E+00 | 1.14E−01 |
| S164G | 1.02E+00 | 1.29E−01 |
| L222I | 6.50E−01 | 1.31E−01 |
| S226T | 6.49E−01 | 1.05E−01 |
| H76Q | 6.37E−01 | 1.06E−01 |
| R242E | 4.45E−01 | 1.24E−01 |
| K19T | 4.18E−01 | 1.13E−01 |
| N249D | 3.38E−01 | 1.03E−01 |

TABLE 6-continued

Mutational contributions (mean) to reduced β-casein 192/193 cleavage and standard deviations (sd) based on statistical analysis.

| mutation | mean | sd |
|---|---|---|
| L166V | 3.07E−01 | 9.43E−02 |
| I96L | 2.93E−01 | 1.02E−01 |
| V309I | 2.08E−01 | 1.23E−01 |

Based on the obtained results it is concluded that mutations shown in table 6 reduce β-casein 192/193 cleavage. Since these mutations cause less generation of the C-terminal fragment of β-casein, β(193-209), they represent preferred mutations in chymosin variants for making cheese with less bitter taste due to reduced cleavage of β-casein.

Multi-Substitution Library 5

Another set of camel chymosin variants, each having multiple substitutions compared to wild type, were generated and analyzed as described above. All variants have an amino acid sequence identical to camel chymosin (mature polypeptide of SEQ ID NO:2), except for the variations mentioned in the table. Camel chymosin (CHY-MAX M) is included as reference.

Clotting activities were determined using the REMCAT method.

TABLE 7

Cleavage of β-casein at position 192/193 of camel chymosin variants 223-269.
Numbers are given in % cleavage of β-casein of wild type camel chymosin (CHY-MAX M).

| variant | mutations | | | | | | | | | β(193-209) |
|---|---|---|---|---|---|---|---|---|---|---|
| CHY-MAX M | | | | | | | | | | 100 |
| 223 | K19T | D59N | I96L | S164G | L222I | G251D | | | | 46 |
| 224 | Y11I | K19T | D59N | I96V | L222I | R242D | G251D | | | 47 |
| 225 | K19S | D59N | I96V | S164G | G251D | | | | | 59 |
| 226 | K19S | I96L | S164G | L166V | L222I | R242E | | | | 20 |
| 227 | K19T | D59N | I96L | S164G | L166V | L222I | R242D | G251D | L253I | 25 |
| 228 | D59N | I96L | S164G | L222I | R242E | L253I | I263L | | | 27 |
| 229 | K19T | D59N | E83T | I96L | L222I | G251D | I263L | | | 65 |
| 230 | Y11I | K19T | D59N | S164G | L222I | G251D | I263V | | | 28 |
| 231 | K19T | D59N | I96L | S164G | L166I | G251D | L253V | | | 44 |
| 232 | K19T | I96V | S164G | L222I | N249D | G251D | L253I | | | 50 |
| 233 | K19T | I96L | L222I | R242E | L253I | | | | | 54 |
| 234 | K19T | E83S | I96L | S164G | L222I | R242E | G251D | L253I | | 21 |
| 235 | D59N | E83T | I96L | S164N | L222V | G251D | | | | 119 |
| 236 | K19S | D59N | I96L | S164G | L222I | R242E | N249E | G251D | | 31 |
| 237 | K19T | I96L | S164G | L166V | L222I | N249D | I263L | | | 32 |
| 238 | D59N | I96L | L166V | L222I | R242E | G251D | | | | 44 |
| 239 | K19T | D59N | E83T | S164G | L166V | L222I | R242D | G251D | | 31 |
| 240 | Y11I | K19T | D59N | E83S | I96L | S164G | L222I | N249D | | 24 |
| 241 | K19T | E83T | I96L | S164G | L222I | R242E | L253V | | | 24 |
| 242 | K19T | D59N | I96L | S164G | L166I | L222I | R242E | N249D | | 28 |
| 243 | Y11V | K19T | D59N | I96L | S164G | L166V | L222I | R242E | G251D | L253I | 17 |
| 244 | K19T | I96L | S164N | L222I | R242E | I263L | | | | 72 |
| 245 | Y11V | D59N | I96L | S164G | L222I | G251D | L253V | | | 30 |
| 246 | K19T | D59N | I96V | S164G | L166V | L222I | R242E | I263L | | 25 |
| 247 | Y11V | K19T | D59N | I96L | S164N | L166I | L222I | G251D | | 67 |
| 248 | K19T | I96L | S164G | L166V | L222I | R242E | N249D | G251D | I263V | 33 |

TABLE 7-continued

Cleavage of β-casein at position 192/193 of camel chymosin variants 223-269.
Numbers are given in % cleavage of β-casein of wild type camel chymosin (CHY-MAX M).

| variant | mutations | | | | | | | | β(193-209) |
|---|---|---|---|---|---|---|---|---|---|
| 249 | K19T | I96L | S164G | R242E | L253I | | | | 42 |
| 250 | K19S | D59N | E83S | I96L | S164N | L222I | G251D | | 84 |
| 251 | K19T | D59N | I96L | S164G | L222V | N249E | G251D | I263V | 40 |
| 252 | K19T | D59N | I96L | S164G | L222I | N249E | G251D | L253V | I263L | 33 |
| 253 | Y11I | K19T | I96L | S164G | L222V | R242E | G251D | | 29 |
| 254 | I96L | S164G | L222I | R242E | N249D | G251D | I263L | | 29 |
| 255 | K19T | D59N | I96L | S164G | L166I | L222I | R242D | G251D | I263V | 28 |
| 256 | K19T | D59N | I96L | S164G | L222V | R242E | N249D | L253I | 42 |
| 257 | H76Q | I96L | S164G | L222I | R242E | G251D | S273Y | | 23 |
| 258 | K19T | E83S | I96L | S164G | L222I | R242E | N249D | G251D | L253I | 22 |
| 259 | I96L | S164G | L166V | L222I | R242E | N249D | I263L | | 34 |
| 260 | Y11V | K19T | E83S | I96L | S164G | L166V | L222I | R242E | G251D | 20 |
| 261 | Y11V | K19T | I96L | S164G | L166V | L222I | R242E | | 30 |
| 262 | Y11V | E83S | I96L | S164G | L222I | R242E | G251D | L253I | I263L | 21 |
| 263 | Y11V | I96L | S164G | L222I | R242E | N249D | L253I | I263L | 23 |
| 264 | K19T | I96L | S164G | L166V | L222I | R242E | N249D | I263L | 35 |
| 265 | Y11V | E83S | I96L | S164G | L222I | R242E | L253I | I263L | 24 |
| 266 | K19T | E83S | I96L | S164G | L166V | L222I | R242E | N249D | G251D | L253I | 26 |
| 267 | I96L | S164G | L222I | R242E | G251D | S274Y | | | 42 |
| 268 | H76Q | I96L | S164G | L222I | R242E | G251D | | | 25 |
| 269 | I96L | S164G | L222I | R242E | G251D | | | | 41 |

In Table 7 are shown camel chymosin variants with data on cleavage of β-casein 192/193. Out of 47 variants, 46 reveal between 16% and 83% reduced proteolytic activity compared to wild type camel chymosin.

Mutational Analysis of Multi-Substitution Library 5

A statistical analysis of the positional and mutational effects on β-casein cleavage was performed based on the proteolytic data of library 5 variants. The most beneficial mutations for decreased β-casein cleavage are shown in table 8.

TABLE 8

Mutational contributions (mean) to reduced β-casein 192/193 cleavage and standard deviations (sd) based on statistical analysis.

| mutation | mean | sd |
|---|---|---|
| S164G | 5.08E−01 | 2.40E−02 |
| R242E | 2.76E−01 | 2.94E−02 |
| Y11V | 2.70E−01 | 2.91E−02 |
| L222I | 2.22E−01 | 2.76E−02 |
| E83S | 2.07E−01 | 3.61E−02 |
| Y11I | 2.04E−01 | 2.91E−02 |
| H76Q | 1.68E−01 | 3.13E−02 |
| D59N | 1.24E−01 | 3.03E−02 |
| L166V | 1.06E−01 | 3.75E−02 |
| R242D | 1.01E−01 | 2.09E−02 |
| L253I | 7.93E−02 | 3.26E−02 |
| L253V | 6.87E−02 | 2.82E−02 |
| K19S | 4.62E−02 | 4.19E−02 |
| I96L | 4.08E−02 | 2.64E−02 |
| I263V | 3.56E−02 | 2.86E−02 |
| E83T | 3.21E−02 | 2.95E−02 |

Based on the obtained results it is concluded that mutations shown in table 8 reduce β-casein 192/193 cleavage.

Since these mutations cause less generation of the C-terminal fragment of β-casein, β(193-209), they represent preferred mutations in chymosin variants for making cheese with less bitter taste due to reduced cleavage of β-casein.

Structure-Based Variations in Camel Chymosin

Variants of camel chymosin (SEQ ID NO:2) were made with amino acid changes in positions determined by protein structural analysis (Tab. 9). Mutations N100Q and N291Q were introduced into both N-glycosylation sites of these variants and the reference camel chymosin (CamUGly) to yield non-glycosylated, homogeneous protein samples.

Clotting activities were determined using the μIMCU method.

TABLE 9

Cleavage of β-casein at position 192/193 of camel chymosin variants 270-308. Numbers are given in % cleavage of non-glycosylated camel chymosin (CamUGly).

| variant | mutations | | | β(193-209) |
|---|---|---|---|---|
| CamUGly | | N100Q | N291Q | 100 |
| 270 | V32L | N100Q | N291Q | 28 |
| 271 | V221K | N100Q | N291Q | 143 |
| 272 | D290E | N100Q | N291Q | 60 |
| 273 | V136I | N100Q | N291Q | 111 |
| 274 | E240Q | N100Q | N291Q | 109 |
| 275 | R242Q | N100Q | N291Q | 74 |
| 276 | G289S | N100Q | N291Q | 51 |
| 277 | N292H | N100Q | N291Q | 164 |
| 278 | L295K | N100Q | N291Q | 131 |
| 279 | V136E | N100Q | N291Q | 99 |
| 280 | D290L | N100Q | N291Q | 58 |
| 281 | F119Y | N100Q | N291Q | 107 |
| 282 | Q280E | N100Q | N291Q | 85 |
| 283 | F282E | N100Q | N291Q | 79 |
| 285 | R254S | N100Q | N291Q | 78 |
| 286 | R242E | N100Q | N291Q | 89 |
| 288 | V203M | N100Q | N291Q | 115 |
| 289 | N249R | N100Q | N291Q | 90 |
| 290 | H56K | N100Q | N291Q | 140 |
| 291 | S74D | N100Q | N291Q | 101 |
| 292 | A131D | N100Q | N291Q | 230 |
| 293 | Y190A | N100Q | N291Q | 28 |
| 294 | I297A | N100Q | N291Q | 185 |
| 295 | H76Q | N100Q | N291Q | 48 |
| 296 | S273Y | N100Q | N291Q | 58 |
| 297 | K19T | N100Q | N291Q | 66 |
| 298 | D59N | N100Q | N291Q | 60 |
| 299 | L222I | N100Q | N291Q | 54 |
| 300 | V309I | N100Q | N291Q | 70 |
| 301 | I96L | N100Q | N291Q | 75 |
| 302 | Y21S | N100Q | N291Q | 67 |
| 303 | L130I | N100Q | N291Q | 29 |
| 304 | S132A | N100Q | N291Q | 28 |
| 305 | S226T | N100Q | N291Q | 44 |
| 306 | G251D | N100Q | N291Q | 88 |

TABLE 9-continued

Cleavage of β-casein at position 192/193 of camel chymosin variants 270-308. Numbers are given in % cleavage of non-glycosylated camel chymosin (CamUGly).

| variant | mutations | | | β(193-209) |
|---|---|---|---|---|
| 307 | Y243E | N100Q | N291Q | 62 |
| 308 | S273D | N100Q | N291Q | 66 |

Based on the results shown in table 9 it is concluded that mutations K19T, Y21S, V32L, D59N, H76Q, I96L, L130I, S132A, Y190A, L222I, S226T, D290E, D290L, R242E, R242Q, Y243E, G251D, R254S, S273D, S273Y, Q280E, F282E, G289S, and V309I reduce cleavage of β-casein 192/193 by more than 10%.

Since these mutations cause less generation of the C-terminal fragment of β-casein, β(193-209), they represent preferred mutations in chymosin variants for making cheese with less bitter taste due to reduced cleavage of β-casein.

Ten out of 24 variants with decreased cleavage of β-casein 192/193 shown in table 9 bear mutations (V32L, H76Q, L130I, S132A, Y190A, L222I, S226T, G289S, D290E, D290L) within or in structural proximity to the substrate binding cleft (FIG. 5), suggesting a direct impact of these mutations on β-casein binding.

Nine out of 24 variants with decreased cleavage of β-casein 192/193 shown in table 9 bear mutations (R242E, R242Q, Y243E, G251D, R254S, S273D, S273Y, Q280E, F282E) in a distinct region on the protein surface that is located in proximity to the binding cleft as seen in FIG. 6. This region has been suggested to support binding of the κ-casein substrate by interacting with its positively charged sequence Arg96 to His102 (references 5, 16-18) in positions P10 to P4 (reference 10). The introduced mutations may strengthen these interactions by reducing the net charge of this region on the protein surface. Increased binding of κ-casein will ultimately inhibit binding and hydrolysis of other substrates such as β-casein. The results show that single amino acid substitutions in this region can increase C/P significantly.

Negative Charge Combinations in Camel Chymosin

More variants of camel chymosin (SEQ ID NO:2) were made with combinations of mutations that introduce negative charges into the surface region described above (R242E, Y243E, G251D, N252D, R254E, S273D, Q280E). Mutations N100Q and N291Q were introduced into both N-glycosylation sites of these variants and the reference camel chymosin (CamUGly) to yield non-glycosylated, homogeneous protein samples (Tab. 10).

Clotting activities were determined using the pIMCU method.

TABLE 10

Cleavage of β-casein at position 192/193 of camel chymosin variants 309-323. Numbers are given in % cleavage of non-glycosylated camel chymosin (CamUGly).

| variant | mutations | | | | | | β(193-209) |
|---|---|---|---|---|---|---|---|
| CamUGly | | | | | N100Q | N291Q | 100 |
| 309 | R242E | Q280E | | | N100Q | N291Q | 50 |
| 310 | R242E | N252D | | | N100Q | N291Q | 65 |
| 311 | N252D | Q280E | | | N100Q | N291Q | 61 |
| 312 | Y243E | Q280E | | | N100Q | N291Q | 59 |
| 313 | Y243E | N252D | | | N100Q | N291Q | 62 |
| 314 | R254E | Q280E | | | N100Q | N291Q | 66 |
| 315 | S273D | Q280E | | | N100Q | N291Q | 85 |
| 316 | R242E | G251D | | | N100Q | N291Q | 92 |
| 317 | R242E | G251D | Q280E | | N100Q | N291Q | 73 |
| 318 | R242E | S273D | Q280E | | N100Q | N291Q | 81 |
| 319 | N252D | S273D | Q280E | | N100Q | N291Q | 89 |
| 320 | G251D | S273D | Q280E | | N100Q | N291Q | 96 |
| 321 | R242E | R254E | Q280E | | N100Q | N291Q | 92 |
| 322 | R242E | R254E | S273D | Q280E | N100Q | N291Q | 72 |
| 323 | Y243E | R254E | S273D | | N100Q | N291Q | 70 |

All variants shown in table 10 reveal decreased β-casein cleavage compared to non-glycosylated camel chymosin. It is concluded that the inhibition of β-casein cleavage by introducing negative charges into the P10-P4 interacting region on the chymosin structure can be further enhanced by combinations of the respective mutations.

Structure-Based Variations in Bovine Chymosin

Variants of bovine chymosin (SEQ ID NO:1) were made with amino acid changes in positions determined by protein structural analysis (Tab. 11). Mutations N252Q and N291Q were introduced into both N-glycosylation sites of these variants and the reference bovine chymosin (BovUGly) to yield non-glycosylated homogeneous protein samples.

Clotting activities were determined using the μIMCU method.

TABLE 11

Cleavage of β-casein at position 192/193 of bovine chymosin variants 325-346. Numbers are given in % cleavage of non-glycosylated bovine chymosin (BovUGly).

| variant | mutations | | | β(193-209) |
|---|---|---|---|---|
| BovUGly | | N252Q | N291Q | 100 |
| 325 | V223F | N252Q | N291Q | 171 |
| 326 | E290D | N252Q | N291Q | 157 |
| 327 | A117S | N252Q | N291Q | 119 |
| 328 | I136V | N252Q | N291Q | 93 |
| 329 | Q242R | N252Q | N291Q | 146 |
| 330 | Q278K | N252Q | N291Q | 139 |
| 331 | S289G | N252Q | N291Q | 145 |
| 333 | Q294E | N252Q | N291Q | 155 |

TABLE 11-continued

Cleavage of β-casein at position 192/193 of bovine chymosin variants 325-346. Numbers are given in % cleavage of non-glycosylated bovine chymosin (BovUGly).

| variant | mutations | | | β(193-209) |
|---|---|---|---|---|
| 335 | D249N | N252Q | N291Q | 171 |
| 336 | D251G | N252Q | N291Q | 143 |
| 337 | G244D | N252Q | N291Q | 103 |
| 338 | Q56H | N252Q | N291Q | 125 |
| 339 | L32I | N252Q | N291Q | 121 |
| 340 | K71E | N252Q | N291Q | 133 |
| 341 | P72T | N252Q | N291Q | 106 |
| 342 | Q83T | N252Q | N291Q | 122 |
| 343 | V113F | N252Q | N291Q | 159 |
| 344 | E133S | N252Q | N291Q | 141 |
| 345 | Y134G | N252Q | N291Q | 105 |
| 346 | K71A | N252Q | N291Q | 123 |

Except I136V, all mutations caused increased cleavage of β-casein 192/193 in the variants shown in table 11. Notably, while substitutions I136V, Q242R, D251G, S289G, and E290D increased β-casein cleavage of bovine chymosin, decreased β-casein cleavage was observed by the respective reverse mutations V136I, R242Q, G251D, G289S, and D290E in camel chymosin (Tab. 9). A similar effect is seen in position 32. While V32L caused decreased β-casein cleavage of camel chymosin, mutation of L32 to I—a β branched hydrophobic amino acid with structural similarity to V—resulted in increased β-casein cleavage of bovine chymosin. This demonstrates that these amino acid changes exert similar effects on chymosin specificity across species.

Variations of the Camel Chymosin N-terminus

Variants of camel chymosin (SEQ ID NO:2) were made with amino acid changes in positions determined by protein structural analysis of the molecular interactions of the N-terminal sequence Y11-D13 within the substrate binding cleft (Tab. 12). Mutations N100Q and N291Q were introduced into both N-glycosylation sites of these variants and the reference camel chymosin (CamUGly) to yield non-glycosylated, homogeneous protein samples.

Clotting activities were determined using the μIMCU method.

TABLE 12

Cleavage of β-casein at position 192/193 of camel chymosin variants 347-366. Numbers are given in % cleavage of non-glycosylated camel chymosin (CamUGly).

| variant | mutations | | | | β(193-209) |
|---|---|---|---|---|---|
| CamUGly | | | N100Q | N291Q | 100 |
| 347 | Y11H | | N100Q | N291Q | 109 |
| 348 | Y11K | | N100Q | N291Q | 126 |
| 349 | Y11R | | N100Q | N291Q | 100 |
| 350 | Y11H | D290E | N100Q | N291Q | 50 |
| 351 | Y11R | D290E | N100Q | N291Q | 40 |
| 352 | Y11F | | N100Q | N291Q | 105 |
| 353 | Y11I | | N100Q | N291Q | 98 |
| 354 | Y11L | | N100Q | N291Q | 93 |
| 356 | L12F | | N100Q | N291Q | 102 |
| 357 | L12I | | N100Q | N291Q | 91 |
| 359 | D13N | | N100Q | N291Q | 127 |
| 360 | D13Q | | N100Q | N291Q | 109 |
| 361 | D13S | | N100Q | N291Q | 131 |
| 362 | D13T | | N100Q | N291Q | 155 |
| 363 | D13F | | N100Q | N291Q | 108 |
| 364 | D13L | | N100Q | N291Q | 120 |
| 365 | D13V | | N100Q | N291Q | 136 |
| 366 | D13Y | | N100Q | N291Q | 124 |

Analysis of the camel chymosin structure guided variations in the N-terminal sequence Y11-D13 as well as in position D290, a potential interaction partner of Y11 (FIG. 7). Since casein substrates compete with the N-terminal chymosin sequence for binding within the binding cleft, amino acid substitutions that change interactions between binding cleft and the motif Y11-D13 are expected to impact enzymatic activity toward various casein substrates and, thus, cleavage of β-casein 192/193. The results of the respective variants 347-366 show strong variation of β-casein cleavage (Tab. 12). Notably, variants 353 and 355—both bearing mutation D290E—reveal decreased β-casein cleavage.

Multi-Substitution Library 6

Another set of camel chymosin variants, each having multiple substitutions compared to wild type, were generated and analyzed as described above. All variants have an amino acid sequence identical to camel chymosin (mature polypeptide of SEQ ID NO:2), except for the variations mentioned in the table. Camel chymosin (CHY-MAX M) is included as reference.

Clotting activities were determined using the pIMCU method.

TABLE 13

Cleavage of β-casein at position 192/193 of camel chymosin variants 367-416. Numbers are given in % cleavage of wild type camel chymosin (CHY-MAX M).

| variant | mutations | | | | | | β(193-209) |
|---|---|---|---|---|---|---|---|
| CHY-MAX M | | | | | | | 100 |
| 367 | R67Q | N100Q | L130I | M157L | V248I | N291Q | 44 |
| 368 | N100Q | L130I | S132A | M157L | K231N | | 24 |
| 369 | R67Q | I96L | L130I | M157L | L222I | M256L | 13 |
| 370 | R67Q | L130I | S132A | M157L | R242E | V248I | 17 |
| 371 | R67Q | N100Q | M157L | R242E | M256L | | 69 |
| 372 | R67Q | G70D | M157L | R242E | V248I | | 60 |
| 373 | V32L | R67Q | M157L | L222I | R242E | | 9 |
| 374 | Y11V | R67Q | M157L | V248I | M256L | | 72 |
| 375 | R67Q | V136I | M157L | L222I | V248I | | 26 |
| 376 | L130I | M157L | V248I | M256L | N291Q | | 28 |
| 377 | R67Q | I96L | L130I | M157L | K231N | R242E | 20 |
| 378 | V32L | R67Q | L130I | M157L | L222I | K231N | 5 |
| 379 | L130I | V136I | M157L | L222I | N292H | | 22 |
| 380 | R67Q | G70D | M157L | L222I | N291Q | | 81 |
| 381 | V32L | R67Q | L130I | K231N | N292H | | 6 |
| 382 | Y11V | R67Q | N100Q | L130I | V136I | M157L | 31 |
| 383 | R67Q | L130I | L222I | R242E | M256L | | 14 |

TABLE 13-continued

Cleavage of β-casein at position 192/193 of camel chymosin variants 367-416. Numbers are given in % cleavage of wild type camel chymosin (CHY-MAX M).

| variant | mutations | | | | | β(193-209) |
|---|---|---|---|---|---|---|
| 384 | R67Q | M157L | L222I | V248I | N292H | 62 |
| 385 | V32L | R67Q | M157L | M256L | N291Q | 12 |
| 386 | R67Q | L130I | S132A | M157L | L222I | N292H | 10 |
| 387 | R67Q | N100Q | L130I | M157L | K231N | N291Q | 47 |
| 388 | R67Q | L130I | K231N | V248I | N291Q | 43 |
| 389 | Y11V | R67Q | L130I | M157L | L222I | K231N | 13 |
| 390 | I45V | L130I | M157L | K231N | R242E | 15 |
| 391 | V32L | R67Q | V136I | M157L | N291Q | 17 |
| 392 | R67Q | N100Q | L130I | D158S | V248I | 32 |
| 393 | I45V | R67Q | L130I | M157L | L222I | K231N | 14 |
| 394 | V32L | R67Q | L130I | S132A | M157L | V248I | 3 |
| 395 | Y11V | R67Q | L130I | M157L | N291Q | N292H | 30 |
| 396 | R67Q | N100Q | L130I | M157L | L222I | K231N | 20 |
| 397 | I45V | R67Q | G70D | L130I | S132A | 18 |
| 398 | I45V | R67Q | L130I | V248I | N292H | 39 |
| 399 | Y11V | R67Q | L130I | M157L | L222I | R242E | 11 |
| 400 | R67Q | N100Q | D158S | L130I | M157L | L222I | 19 |
| 401 | R67Q | L130I | V136I | M157L | K231N | V248I | 25 |
| 402 | I45V | R67Q | L130I | L222I | N291Q | 24 |
| 403 | R67Q | G70D | L130I | M157L | K231N | M256L | 23 |
| 404 | V32L | R67Q | L130I | M157L | D158S | V248I | 5 |
| 405 | R67Q | L130I | M157L | D158S | R242E | N291Q | 30 |
| 406 | R67Q | L130I | M157L | D158S | K231N | N292H | 30 |
| 407 | R67Q | L130I | V248I | M256L | N292H | 42 |
| 408 | V32L | R67Q | I96L | L130I | M157L | V248I | 12 |
| 409 | R67Q | I96L | N100Q | L130I | M157L | N292H | 58 |
| 410 | V32L | R67Q | G70D | N100Q | M157L | 15 |
| 411 | V32L | R67Q | L130I | M157L | K231N | M256L | 32 |
| 412 | R67Q | I96L | M157L | L222I | K231N | 72 |
| 413 | R67Q | M157L | L222I | K231N | V248I | 70 |
| 414 | R67Q | L130I | M157L | R242E | M256L | N292H | 23 |
| 415 | R67Q | L222I | K231N | V248I | 77 |
| 416 | R67Q | S132A | L222I | K231N | R242E | V248I | 13 |

In Table 13 are shown camel chymosin variants with data on cleavage of β-casein 192/193. All 50 variants reveal between 19% and 97% reduced proteolytic activity compared to wild type camel chymosin.

Mutational Analysis of Multi-Substitution Library 6

A statistical analysis of the positional and mutational effects on β-casein cleavage was performed based on the proteolytic data of library 6 variants. The most beneficial mutations for decreased β-casein cleavage are shown in Table 14.

TABLE 14

Mutational contributions (mean) to reduced β-casein 192/193 cleavage and standard deviations (sd) based on statistical analysis.

| mutation | mean | sd |
|---|---|---|
| V32L | 4.19E−01 | 2.43E−02 |
| L130I | 1.92E−01 | 1.47E−02 |
| S132A | 1.88E−01 | 3.28E−02 |
| L222I | 7.39E−02 | 1.09E−02 |
| M157L | 3.28E−02 | 1.47E−02 |
| D158S | 2.50E−02 | 2.08E−02 |
| R67Q | 2.44E−02 | 1.15E−02 |

TABLE 14-continued

Mutational contributions (mean) to reduced β-casein 192/193 cleavage and standard deviations (sd) based on statistical analysis.

| mutation | mean | sd |
|---|---|---|
| Y11V | 2.04E−02 | 8.41E−03 |
| M256L | 2.00E−02 | 1.12E−02 |

Based on the obtained results it is concluded that mutations shown in Table 14 reduce β-casein 192/193 cleavage.

Since these mutations cause less generation of the C-terminal fragment of β-casein, β(193-209), they represent preferred mutations in chymosin variants for making cheese with less bitter taste due to reduced cleavage of β-casein.

Another set of camel chymosin variants, each having multiple substitutions compared to the wild type, were generated and analyzed as described above. All variants have an amino acid sequence identical to camel chymosin (mature polypeptide of SEQ ID NO:2), except for the variations mentioned in the table. Camel chymosin (CHY-MAX M) is included as reference.

Clotting activities were determined using the µIMCU method.

TABLE 15

Cleavage of β-casein at position 192/193 (β), specific clotting (C), proteolysis (P) and C/P ratio of camel chymosin variants 417-461. Numbers are given in % of wild type camel chymosin, CHY-MAX M (CMM).

| variant | mutations | | | | | | | | β | (C) | (P) | C/P |
|---|---|---|---|---|---|---|---|---|---|---|---|---|
| CMM | | | | | | | | | 100 | 100 | 100 | 100 |
| 417 | Y11V | K19T | D59N | S164G | L166V | L222I | R242E | N249E | G251D | 21 | 132 | 20 | 651 |

TABLE 15-continued

Cleavage of β-casein at position 192/193 (β), specific clotting (C), proteolysis (P) and C/P ratio of camel chymosin variants 417-461. Numbers are given in % of wild type camel chymosin, CHY-MAX M (CMM).

| variant | | | | mutations | | | | | | | β | (C) | (P) | C/P |
|---|---|---|---|---|---|---|---|---|---|---|---|---|---|---|
| 418 | Y11V | K19T | D59N | I96L | S164G | L166I | L222I | R242E | N249E | G251D | | 18 | 114 | 21 | 556 |
| 419 | Y11I | K19T | D59N | I96L | S164G | L166V | L222I | R242E | N249E | G251D | | 17 | 108 | 20 | 554 |
| 420 | Y11I | K19T | D59N | I96L | S164G | L166I | L222I | R242E | G251D | | | 18 | 98 | 11 | 898 |
| 421 | Y11V | K19T | D59N | I96L | L166V | L222V | R242E | N249E | G251D | L253I | | 36 | 132 | 84 | 156 |
| 422 | Y11V | K19T | D59N | I96L | S164G | L166V | R242E | | | | | 38 | 105 | 13 | 802 |
| 423 | Y11V | K19T | D59N | I96L | S164G | L222V | R242E | G251D | | | | 28 | 89 | 8 | 1131 |
| 424 | Y11V | K19T | D59N | I96L | S164G | L166I | R242E | N249E | G251D | L253I | | 20 | 93 | 8 | 1111 |
| 425 | Y11V | K19T | D59N | I96L | S164G | L166V | L222V | R242E | N249E | G251D | | 21 | 105 | 18 | 572 |
| 426 | Y11V | K19T | D59N | I96L | S164G | L166I | L222V | R242E | N249E | G251D | L253I | 16 | 93 | 18 | 512 |
| 427 | Y11V | K19T | D59N | L166V | L222I | R242E | N249E | G251D | L253I | | | 33 | 137 | 42 | 323 |
| 428 | Y11V | K19T | D59N | I96L | S164G | L166V | L222I | R242E | N249E | | | 20 | 120 | 15 | 803 |
| 429 | Y11V | K19T | D59N | S164G | L166I | L222I | R242E | G251D | | | | 25 | 107 | 17 | 630 |
| 430 | Y11V | K19T | D59N | I96L | S164G | R242E | G251D | | | | | 25 | 89 | 11 | 801 |
| 431 | Y11V | D59N | I96L | S164G | L166I | L222V | R242E | G251D | L253I | | | 23 | 79 | 28 | 283 |
| 432 | Y11V | D59N | I96L | S164G | L166I | L222I | R242E | G251D | | | | 16 | 102 | 24 | 432 |
| 433 | Y11I | D59N | I96L | S164G | L166V | R242E | G251D | L253I | | | | 17 | 97 | 25 | 392 |
| 434 | Y11V | K19T | D59N | I96L | S164G | L222I | R242E | N249E | G251D | | | 17 | 99 | 33 | 301 |
| 435 | Y11V | K19T | D59N | I96L | S164G | L166I | L222V | R242E | G251D | | | 25 | 88 | 17 | 514 |
| 436 | Y11V | K19T | D59N | I96L | S164G | L166V | L222V | R242E | N249E | L253I | | 20 | 95 | 10 | 949 |
| 437 | Y11V | K19T | D59N | I96L | S164G | L166I | L222V | R242E | N249E | G251D | | 20 | 114 | 22 | 520 |
| 438 | Y11I | K19T | I96L | S164G | L166V | R242E | N249E | G251D | | | | 30 | 93 | 7 | 1262 |
| 439 | Y11V | K19T | D59N | I96L | S164G | L166V | L222V | R242E | G251D | | | 25 | 108 | 26 | 423 |
| 440 | Y11V | K19T | D59N | I96L | S164G | L222V | R242E | N249E | G251D | | | 26 | 105 | 9 | 1196 |
| 441 | Y11I | K19T | L222V | R242E | N249E | G251D | | | | | | 46 | 122 | 26 | 469 |
| 442 | Y11V | K19T | I96L | L222V | R242E | N249E | G251D | | | | | 47 | 105 | 21 | 503 |
| 443 | Y11I | K19T | D59N | I96L | S164G | L166V | L222V | R242E | N249E | G251D | | 18 | 105 | 18 | 595 |
| 444 | Y11V | K19T | I96L | S164G | L222V | R242E | N249E | G251D | | | | 22 | 96 | 8 | 1242 |
| 445 | Y11I | K19T | D59N | I96L | S164G | L166I | L222V | R242E | N249E | G251D | | 19 | 82 | 12 | 707 |
| 446 | Y11I | I96L | S164G | L166V | L222V | R242E | N249E | G251D | | | | 21 | 95 | 16 | 579 |
| 447 | Y11I | K19T | D59N | I96L | S164G | L222V | R242E | N249E | | | | 23 | 90 | 11 | 790 |
| 448 | Y11I | K19T | D59N | I96L | S164G | L222V | R242E | N249E | G251D | | | 33 | 153 | 40 | 381 |
| 449 | Y11I | K19T | D59N | I96L | S164G | L222I | R242E | | | | | 18 | 89 | 16 | 564 |
| 450 | Y11I | K19T | D59N | I96L | S164G | L166V | R242E | G251D | | | | 27 | 88 | 5 | 1686 |
| 451 | Y11I | K19T | D59N | S164G | L166I | L222V | R242E | G251D | | | | 27 | 93 | 21 | 440 |
| 452 | Y11I | I96L | L222V | R242E | N249E | G251D | | | | | | 52 | 122 | 22 | 566 |
| 453 | Y11I | I96L | S164G | L222I | R242E | | | | | | | 15 | 74 | 5 | 1375 |
| 454 | Y11V | K19T | I96L | L166V | L222V | R242E | G251D | | | | | 38 | 119 | 52 | 228 |
| 455 | Y11I | D59N | I96L | S164G | L222I | R242E | G251D | | | | | 17 | 105 | 9 | 1139 |
| 456 | Y11I | D59N | I96L | S164G | L222V | R242E | N249E | G251D | | | | 23 | 95 | 15 | 615 |
| 457 | Y11I | K19T | D59N | I96L | S164G | L222I | R242E | N249E | G251D | | | 20 | 101 | 7 | 1419 |
| 458 | Y11I | D59N | I96L | S164G | L166V | R242E | G251D | | | | | 22 | 89 | 16 | 572 |
| 459 | Y11V | K19T | D59N | I96L | L222V | R242E | G251D | | | | | 42 | 143 | 62 | 230 |
| 460 | Y11I | K19T | S164G | L166I | L222V | R242E | N249E | G251D | | | | 23 | 80 | 13 | 625 |
| 461 | Y11I | D59N | I96L | S164G | L166V | L222V | R242E | N249E | G251D | | | 20 | 96 | 35 | 273 |

In Table 15 are shown camel chymosin variants with data on cleavage of β-casein 192/193. All 45 variants show reduced proteolytic activity compared to wild type camel chymosin.

REFERENCES

1. A. Kumar, S. Grover, J. Sharma, V. K. Batish, *Crit. Rev. Biotechnol.* 2010, 30, 243-258.
2. M. W. Børsting, K. B. Qvist, M. Rasmussen, J. Vindeløv, F. K. Vogensen, Y. Ardö, *Dairy Sci.* 2012, 92, 593-612.
3. K. Kastberg Møller, F. P. Rattray, Y. Ardö, *J. Agric. Food Chem.* 2012, 60, 11421-11432.
4. P. L. H. McSweeney, *Int. J. Dairy Technol.* 2004, 57, 127-144.
5. J. Langholm Jensen, A. Mølgaard, J.-C. Navarro Poulsen, M. K. Harboe, J. B. Simonsen, A. M. Lorentzen, K. Hjernø, J. M. van den Brink, K. B. Qvist, S. Larsen, *Acta Cryst.* 2013, D69, 901-913.
6. S. Chitpinityol, D. Goode, M. J. C. Crabbe, *Food Chem.* 1998, 62, 133-139.
7. G. L. Gilliland, E. L. Winborne, J. Nachman, A. Wlodawer, *Proteins* 1990, 8, 82-101.
8. D. S. Palmer, A. U. Christensen, J. Sørensen, L. Celik, K. Bruun Qvist, B. Schiøtt, *Biochemistry* 2010, 49, 2563-2573.
9. J. Sørensen, D. S. Palmer, B. Schiøtt, *J. Agric. Food Chem.* 2013, 61, 7949-7959.
10. I. Schechter, A. Berger, *Biochem. Biophys. Res. Commun.* 1967, 425, 497-502.
11. L. K. Creamer, N. F. Olsen, J. Food Sci. 1982, 47:631-636
12. N. Bansal, M. A. Drake, P. Piraino, M. L. Broe, M. Harboe, P. F. Fox, P. L. H. McSweeney, Int. Dairy J. 2009, 19:510-517.
13. A. C. Moynihan, S. Govindasamy-Lucey, J. J. Jaeggi, M. E. Johnson, J. A. Lucey, P. L. H. McSweeney, J. Dairy Sci. 2014, 97:85-96.
14. J. Ehren, S. Govindarajan, B. Moron, J. Minshull, C. Khosla, *Prot. Eng. Des. Sel.* 2008, 21, 699-707.
15. S. Govindarajan, B. Mannervik, J. A. Silverman, K. Wright, D. Regitsky, U. Hegazy, T. J. Purcell, M. Welch, J. Minshull, C. Gustafsson, *ACS Synth. Biol.* 2015, 4, 221-227.
16. M. Newman, M. Safro, C. Frazao, G. Khan, A. Zdanov, I. J. Tickle, T. L. Blundell, N. Andreeva, *J. Mol. Biol.* 1991, 221, 1295-1309.

17. E. Gustchina, L. Rumsh, L. Ginodman, P. Majer, N. Andreeva, *FEBS Lett.* 1996, 379, 60-62.

18. S. Visser, C. J. Slangen, P. J. van Rooijen, *Biochem. J.* 1987, 244, 553-558.

---

The invention claimed is:

1. An isolated chymosin polypeptide variant, wherein:
   (a) the isolated chymosin polypeptide variant has a specific clotting activity (IMCU/mg total protein) that is at least 70% of the specific clotting activity of isolated camel chymosin polypeptide having SEQ ID NO:4;
   (b) the isolated chymosin polypeptide variant cleaves β-casein with a frequency of less than 50% of the frequency of β-casein cleavage by the isolated camel chymosin polypeptide having SEQ ID NO:4, as determined by quantifying β-casein peptides obtained by incubating skim milk with the chymosin variant or the camel chymosin, wherein quantification is carried out by RP-HPLC coupled to an ESI-Q-TOF mass spectrometer;
   (c) the isolated chymosin polypeptide variant comprises an amino acid sequence comprising from 3 to fewer than 30 amino acid alterations as compared to the amino acid sequence of SEQ ID NO: 4; and
(d) the isolated chymosin polypeptide variant comprises an L222V substitution relative to SEQ ID NO:4.

2. The isolated chymosin polypeptide variant of claim 1, wherein the polypeptide variant has at least 75% of the specific clotting activity of the isolated camel chymosin polypeptide having SEQ ID NO:4.

3. The isolated chymosin polypeptide variant of claim 1, wherein the polypeptide variant exhibits unspecific proteolytic activity (P) that is less than 50% that of the isolated camel chymosin polypeptide having SEQ ID NO:4.

4. The isolated chymosin polypeptide variant of claim 1, wherein the polypeptide variant has a clotting activity to proteolytic activity (C/P) ratio of at least 300% of the C/P ratio of the isolated camel chymosin polypeptide having SEQ ID NO:4.

5. The isolated chymosin polypeptide variant of claim 1, wherein, in addition to the L222V substitution, the variant further comprises one or more amino acid substitutions at a position relative to SEQ ID NO:4 selected from: L130, S132, V32, S226, V221, S255, S277, L253, M157, S271, H76, V183, I263, T239, Y307, R67, G251, R61, E83, D59, S273, Y21, V203, E294, G289, T284, Y127, V248, K321, V205, R316, D158, L166, R242 and I96.

6. The isolated chymosin polypeptide variant of claim 1, wherein, in addition to the L222V substitution, the variant further comprises one or more amino acid substitutions relative to SEQ ID NO:4 selected from: R266V, L12M, V260T, V51L, Q288E, E83S, G251W, S154A, L180I, L215V, D144Q, I303L, L105E, K321P, E262T, and R242E.

7. A method for making an isolated chymosin polypeptide variant according to claim 1, comprising:
(a) making an alteration at from 3 to fewer than 30 positions in a DNA sequence encoding the polypeptide of SEQ ID NO:4 to obtain a DNA sequence encoding the chymosin polypeptide variant, wherein the variant comprises a L222V substitution relative to SEQ ID NO:4; and
(b) producing and isolating the chymosin polypeptide variant.

8. The method of claim 7, wherein, in addition to the L222V substitution, the polypeptide variant further comprises one or more of the following substitutions relative to SEQ ID NO:4: R266V, L12M, V260T, V51L, Q288E, E83S, G251W, S154A, L180I, L215V, D144Q, I303L, L105E, K321P, E262T, and R242E.

9. A method for making a food or feed product comprising adding an effective amount of the isolated chymosin polypeptide variant according to claim 1 to the food or feed ingredient(s) and carrying our further manufacturing steps to obtain the food or feed product.

10. The method according to claim 9, wherein the food or feed product is a milk-based product.

11. A food or feed product comprising a chymosin polypeptide variant according to claim 1.

12. The method of claim 9, wherein the food or feed product is a cheese.

13. The method of claim 9, wherein the food or feed product is selected from pasta filata, cheddar cheese, continental type cheeses, soft cheese or white brine cheese.

14. The method of claim 12, wherein the method is effective to reduce bitterness in the cheese.

15. The isolated chymosin polypeptide variant of claim 1, wherein, in addition to the L222V substitution, the variant further comprises one or more amino acid substitutions relative to SEQ ID NO:4 selected from: L130I, S132A, V32L, S226T, V221M, S255Y, S277N, L253I, M157L, S271P, H76Q, V183I, I263L, T239S, Y307F, R67Q, G251D, R61Q, D59N, S273Y, Y21S, V203A, E294Q, G289S, T284S, Y127F, V248I, V205I, K231N, R316L, M256L, D158S, L166V, and I96L.

16. The isolated chymosin polypeptide variant of claim 1, wherein, in addition to the L222V substitution, the variant further comprises an amino acid substitution at position S164 relative to SEQ ID NO:4.

17. The isolated chymosin polypeptide variant of claim 1, wherein, in addition to the L222V substitution, the variant further comprises the amino acid substitution S164G relative to SEQ ID NO:4.

18. The isolated chymosin polypeptide variant of claim 1, wherein the variant comprises substitutions relative to SEQ ID NO:4 selected from:
K19T+D59N+I96L+S164G+L222V+N249E+G251D+I263V;
Y11I+K19T+I96L+S164G+L222V+R242E+G251D;
K19T+D59N+I96L+S164G+L222V+R242E+N249D+L253I;
Y11V+K19T+D59N+I96L+L166V+L222V+R242E+N249E+G251D+L253I;
Y11V+K19T+D59N+I96L+S164G+L222V+R242E+G251D;
Y11V+K19T+D59N+I96L+S164G+L166V+L222V+R242E+N249E+G251D;
Y11V+K19T+D59N+I96L+S164G+L166I+L222V+R242E+N249E+G251D+L253I;
Y11V+D59N+I96L+S164G+L166I+L222V+R242E+G251D+L253I;
Y11I+D59N+I96L+S164G+L166V+L222V+R242E+G251D+L253I;
Y11V+K19T+D59N+I96L+S164G+L166I+L222V+R242E+G251D;
Y11I+K19T+D59N+I96L+S164G+L166V+L222V+R242E+N249E+L253I;
Y11V+K19T+D59N+I96L+S164G+L166I+L222V+R242E+N249E+G251D;
Y11V+K19T+D59N+I96L+S164G+L166V+L222V+R242E+G251D;
Y11V+K19T+D59N+I96L+S164G+L222V+R242E+N249E+G251D;
Y11I+K19T+L222V+R242E+N249E+G251D;
Y11V+K19T+I96L+L222V+R242E+N249E+G251D;
Y11I+K19T+D59N+I96L+S164G+L166V+L222V+R242E+N249E+G251D;
Y11V+K19T+I96L+S164G+L166V+L222V+R242E+N249E+G251D;
Y11I+K19T+D59N+I96L+S164G+L166I+L222V+R242E+N249E+G251D;
Y11I+I96L+S164G+L166V+L222V+R242E+N249E+G251D;
Y11I+K19T+D59N+I96L+S164G+L222V+R242E+N249E;
Y11I+K19T+D59N+I96L+L222V+R242E+N249E+G251D;
Y11I+K19T+D59N+S164G+L166I+L222V+R242E+G251D;
Y11V+K19T+I96L+L166V+L222V+R242E+G251D;
Y11I+D59N+I96L+S164G+L222V+R242E+N249E+G251D;
Y11I+D59N+I96L+S164G+L166V+L222V+R242E+G251D;
Y11V+K19T+D59N+I96L+L222V+R242E+G251D;
Y11I+K19T+S164G+L166I+L222V+R242E+N249E+G251D, and

Y11I+D59N+I96L+S164G+L166V+L222V+R242E+
N249E+G251D.

19. The isolated chymosin polypeptide variant of claim 1, wherein the variant comprises substitutions relative to SEQ ID NO:4 selected from:

Y11V+K19T+D59N+I96L+S164G+L222V+R242E+
G251D;

Y11V+K19T+D59N+I96L+S164G+L222V+R242E+
N249E+G251D;

Y11V+K19T+I96L+S164G+L166V+L222V+R242E+
N249E+G251D; and

Y11I+K19T+D59N+I96L+S164G+L222V+R242E+
N249E.

20. A method for making a food or feed product, comprising adding an effective amount of the isolated chymosin polypeptide variant according to claim 18 to the food or feed ingredient(s).

21. The method according to claim 20, wherein the food or feed product is a cheese.

22. A food or feed product comprising a chymosin polypeptide variant according to claim 18.

23. The food or feed product according to claim 22, wherein the food or feed product is a cheese.

24. A method for making an isolated chymosin polypeptide variant according to claim 18, comprising:
(a) making alterations in a DNA sequence encoding the polypeptide of SEQ ID NO:4 to obtain a DNA sequence encoding the chymosin polypeptide variant, and
(b) producing and isolating the chymosin polypeptide variant.

* * * * *

SEQUENCE LISTING

<160> NUMBER OF SEQ ID NOS: 4

<210> SEQ ID NO 1
<211> LENGTH: 381
<212> TYPE: PRT
<213> ORGANISM: Bovine

<400> SEQUENCE: 1

```
Met Arg Cys Leu Val Val Leu Leu Ala Val Phe Ala Leu Ser Gln Gly
 1               5                  10                  15

Ala Glu Ile Thr Arg Ile Pro Leu Tyr Lys Gly Lys Ser Leu Arg Lys
            20                  25                  30

Ala Leu Lys Glu His Gly Leu Leu Glu Asp Phe Leu Gln Lys Gln Gln
        35                  40                  45

Tyr Gly Ile Ser Ser Lys Tyr Ser Gly Phe Gly Glu Val Ala Ser Val
    50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
                85                  90                  95

Asp Phe Trp Val Pro Ser Ile Tyr Cys Lys Ser Asn Ala Cys Lys Asn
            100                 105                 110

His Gln Arg Phe Asp Pro Arg Lys Ser Ser Thr Phe Gln Asn Leu Gly
        115                 120                 125

Lys Pro Leu Ser Ile His Tyr Gly Thr Gly Ser Met Gln Gly Ile Leu
    130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Ile Pro Val Phe Asp Asn Met Met Asn Arg His Leu Val Ala Gln
        195                 200                 205

Asp Leu Phe Ser Val Tyr Met Asp Arg Asn Gly Gln Glu Ser Met Leu
    210                 215                 220

Thr Leu Gly Ala Ile Asp Pro Ser Tyr Tyr Thr Gly Ser Leu His Trp
225                 230                 235                 240

Val Pro Val Thr Val Gln Gln Tyr Trp Gln Phe Thr Val Asp Ser Val
                245                 250                 255

Thr Ile Ser Gly Val Val Ala Cys Glu Gly Gly Cys Gln Ala Ile
            260                 265                 270

Leu Asp Thr Gly Thr Ser Lys Leu Val Gly Pro Ser Ser Asp Ile Leu
        275                 280                 285

Asn Ile Gln Gln Ala Ile Gly Ala Thr Gln Asn Gln Tyr Gly Glu Phe
    290                 295                 300

Asp Ile Asp Cys Asp Asn Leu Ser Tyr Met Pro Thr Val Val Phe Glu
305                 310                 315                 320

Ile Asn Gly Lys Met Tyr Pro Leu Thr Pro Ser Ala Tyr Thr Ser Gln
                325                 330                 335

Asp Gln Gly Phe Cys Thr Ser Gly Phe Gln Ser Glu Asn His Ser Gln
            340                 345                 350
```

Lys Trp Ile Leu Gly Asp Val Phe Ile Arg Glu Tyr Tyr Ser Val Phe
                355                 360                 365

Asp Arg Ala Asn Asn Leu Val Gly Leu Ala Lys Ala Ile
        370                 375                 380

<210> SEQ ID NO 2
<211> LENGTH: 381
<212> TYPE: PRT
<213> ORGANISM: Camelus

<400> SEQUENCE: 2

Met Arg Cys Leu Val Val Leu Leu Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
            35                  40                  45

Tyr Ala Val Ser Ser Lys Tyr Ser Ser Leu Gly Lys Val Ala Arg Glu
50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Val Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Met Glu Gly Phe Leu
130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
210                 215                 220

Thr Leu Gly Ala Ile Asp Pro Ser Tyr Tyr Thr Gly Ser Leu His Trp
225                 230                 235                 240

Val Pro Val Thr Leu Gln Gln Tyr Trp Gln Phe Thr Val Asp Ser Val
                245                 250                 255

Thr Ile Asn Gly Val Ala Val Ala Cys Val Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
290                 295                 300

Asp Val Asn Cys Gly Asn Leu Arg Ser Met Pro Thr Val Phe Glu
305                 310                 315                 320

Ile Asn Gly Arg Asp Tyr Pro Leu Ser Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365

Asp Arg Ala Asn Asn Arg Val Gly Leu Ala Lys Ala Ile
        370                 375                 380

<210> SEQ ID NO 3
<211> LENGTH: 323
<212> TYPE: PRT
<213> ORGANISM: Bos

<400> SEQUENCE: 3

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30

Phe Asp Thr Gly Ser Ser Asp Phe Trp Val Pro Ser Ile Tyr Cys Lys
        35                  40                  45

Ser Asn Ala Cys Lys Asn His Gln Arg Phe Asp Pro Arg Lys Ser Ser
    50                  55                  60

Thr Phe Gln Asn Leu Gly Lys Pro Leu Ser Ile His Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
        115                 120                 125

Ser Leu Ala Ser Glu Tyr Ser Ile Pro Val Phe Asp Asn Met Met Asn
    130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

Phe Thr Val Asp Ser Val Thr Ile Ser Gly Val Val Ala Cys Glu
        195                 200                 205

Gly Gly Cys Gln Ala Ile Leu Asp Thr Gly Thr Ser Lys Leu Val Gly
    210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
            260                 265                 270

Ser Ala Tyr Thr Ser Gln Asp Gln Gly Phe Cys Thr Ser Gly Phe Gln
        275                 280                 285

Ser Glu Asn His Ser Gln Lys Trp Ile Leu Gly Asp Val Phe Ile Arg
    290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 4

```
<211> LENGTH: 323
<212> TYPE: PRT
<213> ORGANISM: Camelus

<400> SEQUENCE: 4

Gly Lys Val Ala Arg Glu Pro Leu Thr Ser Tyr Leu Asp Ser Gln Tyr
1               5                   10                  15

Phe Gly Lys Ile Tyr Ile Gly Thr Pro Pro Gln Glu Phe Thr Val Val
            20                  25                  30

Phe Asp Thr Gly Ser Ser Asp Leu Trp Val Pro Ser Ile Tyr Cys Lys
        35                  40                  45

Ser Asn Val Cys Lys Asn His His Arg Phe Asp Pro Arg Lys Ser Ser
    50                  55                  60

Thr Phe Arg Asn Leu Gly Lys Pro Leu Ser Ile His Tyr Gly Thr Gly
65                  70                  75                  80

Ser Met Glu Gly Phe Leu Gly Tyr Asp Thr Val Thr Val Ser Asn Ile
                85                  90                  95

Val Asp Pro Asn Gln Thr Val Gly Leu Ser Thr Glu Gln Pro Gly Glu
            100                 105                 110

Val Phe Thr Tyr Ser Glu Phe Asp Gly Ile Leu Gly Leu Ala Tyr Pro
        115                 120                 125

Ser Leu Ala Ser Glu Tyr Ser Val Pro Val Phe Asp Asn Met Met Asp
    130                 135                 140

Arg His Leu Val Ala Arg Asp Leu Phe Ser Val Tyr Met Asp Arg Asn
145                 150                 155                 160

Gly Gln Gly Ser Met Leu Thr Leu Gly Ala Ile Asp Pro Ser Tyr Tyr
                165                 170                 175

Thr Gly Ser Leu His Trp Val Pro Val Thr Leu Gln Gln Tyr Trp Gln
            180                 185                 190

Phe Thr Val Asp Ser Val Thr Ile Asn Gly Val Ala Val Ala Cys Val
        195                 200                 205

Gly Gly Cys Gln Ala Ile Leu Asp Thr Gly Thr Ser Val Leu Phe Gly
    210                 215                 220

Pro Ser Ser Asp Ile Leu Lys Ile Gln Met Ala Ile Gly Ala Thr Glu
225                 230                 235                 240

Asn Arg Tyr Gly Glu Phe Asp Val Asn Cys Gly Asn Leu Arg Ser Met
                245                 250                 255

Pro Thr Val Val Phe Glu Ile Asn Gly Arg Asp Tyr Pro Leu Ser Pro
            260                 265                 270

Ser Ala Tyr Thr Ser Lys Asp Gln Gly Phe Cys Thr Ser Gly Phe Gln
        275                 280                 285

Gly Asp Asn Asn Ser Glu Leu Trp Ile Leu Gly Asp Val Phe Ile Arg
    290                 295                 300

Glu Tyr Tyr Ser Val Phe Asp Arg Ala Asn Asn Arg Val Gly Leu Ala
305                 310                 315                 320

Lys Ala Ile
```